United States Patent
Nelson et al.

(10) Patent No.: US 9,822,343 B2
(45) Date of Patent: Nov. 21, 2017

(54) METHODS AND MATERIALS FOR OBTAINING INDUCED PLURIPOTENT STEM CELLS

(75) Inventors: Timothy J. Nelson, Rochester, MN (US); Andre Terzic, Rochester, MN (US); Almudena J. Martinez Fernandez, Rochester, MN (US); Clifford D. Folmes, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 640 days.

(21) Appl. No.: 14/239,980

(22) PCT Filed: Aug. 21, 2012

(86) PCT No.: PCT/US2012/051751
§ 371 (c)(1),
(2), (4) Date: Apr. 16, 2014

(87) PCT Pub. No.: WO2013/028702
PCT Pub. Date: Feb. 28, 2013

(65) Prior Publication Data
US 2014/0227736 A1  Aug. 14, 2014

Related U.S. Application Data

(60) Provisional application No. 61/526,066, filed on Aug. 22, 2011.

(51) Int. Cl.
| | | |
|---|---|---|
| A61K 38/24 | (2006.01) | |
| C07H 21/04 | (2006.01) | |
| C07K 14/00 | (2006.01) | |
| C12N 5/00 | (2006.01) | |
| C12N 15/63 | (2006.01) | |
| C12N 5/074 | (2010.01) | |
| G01N 33/50 | (2006.01) | |

(52) U.S. Cl.
CPC ....... *C12N 5/0696* (2013.01); *G01N 33/5005* (2013.01); *C07H 21/04* (2013.01); *C12N 15/63* (2013.01); *C12N 2500/34* (2013.01); *C12N 2501/602* (2013.01); *C12N 2501/603* (2013.01); *C12N 2501/604* (2013.01); *C12N 2501/606* (2013.01); *C12N 2506/00* (2013.01); *C12N 2506/1307* (2013.01); *C12N 2510/00* (2013.01)

(58) Field of Classification Search
CPC ............... A61K 35/545; C12N 5/0696; C12N 2501/602; C12N 2506/1307; C12N 2506/45; C12N 5/0678; C12N 2501/603; C12N 2501/604; C12N 2501/606; C12N 5/0606; C12N 5/0623; C12N 2501/605; C12N 2501/608; C12N 2506/094; C12N 2506/1384; C12N 2506/28; C12N 5/0656; C12N 5/0662; C12N 15/63; C12N 2502/00; C12N 5/0018; C12N 5/0081; C12N 2506/00; C12N 2500/34; C12N 2500/602; C12N 2500/603; C12N 2500/604; C12N 2500/606; C07H 21/04
USPC ......... 435/377, 455; 530/350, 399; 536/23.5
See application file for complete search history.

(56) References Cited

U.S. PATENT DOCUMENTS

| | | | |
|---|---|---|---|
| 2013/0210138 A1* | 8/2013 | Thomson ............. | C12N 5/0696 435/366 |
| 2014/0227736 A1 | 8/2014 | Nelson | |

FOREIGN PATENT DOCUMENTS

| | | |
|---|---|---|
| WO | WO 2010/017562 | 2/2010 |
| WO | WO 2010/124143 | 10/2010 |

OTHER PUBLICATIONS

Ludwig et al. Derivation of human embryonic stem cells in defined conditions. Nature Biotech, 2006, vol. 24, pp. 185-187 and Supplemental Table S1. (Ludwig with Table 1A).*
Stadtfeld et al. Induced pluripotent stem cells generated without viral integration. Science, vol. 322. pp. 945-949.*
Gonzales et al. Generation of mouse-induced pluripotent stem cells by transient expression of a single nonviral polycistronic vector. PNAS, 2009, vol. 106, pp. 8918-8922.*
Yamanaka. Induction of pluripotent stem cells from mouse fibroblasts by four transcription factors. Cell Prolif., 2008, vol. 41, (Suppl. 1), pp. 51-56.*
Rodriguez et al. Manipulation of OCT4 Levels in Human Embryonic Stem Cells Results in Induction of Differential Cell Types. Experimental Biology and Medicine, 2007, vol. 232, pp. 1368-1380.*
Strelchenko et al. Embryonic Stem Cells from Morula, Methods in Enzymology, 2006, vol. 418, pp. 93-108.*
Esstentials of Stem Cell Biology, R. Lanza et al. Ed., 2006, Elsevier Academic Press, pp. 266-267.*
Sun et al. Feeder-free derivation of induced pluripotent stem cells from adult human adipose stem cells. PNAS, vol. 106, pp. 15720-15725.*
Ludwig et al. Derivation of human embryonic stem cells in defined conditions. Nature Biotech, 2006, vol. 24, pp. 185-187 and Supplemental Table SI. (Ludwig with Table 1A).*
Kahler et al., 2011, US 20110306516 A1, effective filing date, Jun. 15, 2010.*

(Continued)

*Primary Examiner* — Shin Lin Chen
(74) *Attorney, Agent, or Firm* — Fish & Richardson P.C.

(57) ABSTRACT

This document provides methods and materials involved obtaining induced pluripotent stem (iPS) cells. For example, methods and materials for increasing the efficiency for making iPS cells as well as methods and materials for selecting iPS cells are provided.

3 Claims, 9 Drawing Sheets

(56) References Cited

OTHER PUBLICATIONS

Piccoli et al., "Characterization of mitochondrial and extra-mitochondrial oxygen consuming reactions in human hematopoietic stem cells. Novel evidence of the occurrence of NAD(P)H oxidase activity," J Biol Chem., 280 (28):26467-26476, Epub May 9, 2005.
San Martin et al., "Mitochondria determine the differentiation potential of cardiac mesoangioblasts," Stem Cells., 29 (7):1064-1074, Jul. 2011.
Varum et al., "Energy metabolism in human pluripotent stem cells and their differentiated counterparts," PLoS One., 6 (6):e20914, 15 pages, Epub Jun. 17, 2011.
Varum et al., "Enhancement of human embryonic stem cell pluripotency through inhibition of the mitochondrial respiratory chain," Stem Cell Res., 3(2-3):142-156, Epub Aug. 3, 2009.
Yanes et al., "Metabolic oxidation regulates embryonic stem cell differentiation," Nat Chem Biol., 6(6):411-417, Epub May 2, 2010.
International Search Report and Written Opinion in International Application No. PCT/US2012/051751, dated Oct. 25, 2012, 9 pages.
International Preliminary Report on Patentability in International Application No. PCT/US2012/051751, dated Feb. 25, 2014, 7 pages.
Anokye-Danso et al., "Highly efficient miRNA-mediated reprogramming of mouse and human somatic cells to pluripotency," Cell Stem Cell, 2011, 8(4):376-88.
Armstrong et al., "Human induced pluripotent stem cell lines show similar stress defense mechanisms and mitochondrial regulation to human embryonic stem cells," Stem Cells, 2010, 28:661-673.
Arrell et al., "Pharmacoproteomics: advancing the efficacy and safety of regenerative therapeutics," Clin. Pharmacol. Ther., 2007, 82:316-310.
Arrell et al., "Cardioinductive network guiding stem cell differentiation revealed by proteomic cartography of tumor necrosis factor alpha-primed endodermal secretome," Stem Cells, 2008, 26:387-400.
Arrell et al., "ATP-sensitive K+ channel knockout induces cardiac proteome remodeling predictive of heart disease susceptibility," J. Proteome Res., 2009, 8:4823-4834.
Beckonert et al., "Metabolic profiling, metabolomic and metabonomic procedures for NMR spectroscopy of urine, plasma, serum and tissue extracts," Nat Protoc., 2007, 2:2692-2703.
Cho et al., "Dynamic changes in mitochondrial biogenesis and antioxidant enzymes during the spontaneous differentiation of human embryonic stem cells," Biochem. Biophys. Res. Commun., 2006, 348:1472-1478.
Chung et al., "Glycolytic network restructuring integral to the energetics of embryonic stem cell cardiac differentiation," J. Mol. Cell. Cardiol., 2010, 48:725-734.
Chung et al., "Developmental restructuring of the creatine kinase system integrates mitochondrial energetics with stem cell cardiogenesis," Ann. N. Y. Acad. Sci., 2008, 1147:254-263.
Chung et al., "Mitochondrial oxidative metabolism is required for the cardiac differentiation of stem cells," Nat. Clin. Pract. Cardiovasc. Med., 2007, 4(Suppl 1):S60-67.
Dang, "The interplay between MYC and HIF in the Warburg effect," Ernst Schering Found Symp Proc., 2007, 35-53.
DeBerardinis et al., "The biology of cancer: metabolic reprogramming fuels cell growth and proliferation," Cell Metab., 2008, 7:11-20.
Ezashi et al., "Low O2 tensions and the prevention of differentiation of hES cells," Proc Natl Acad Sci USA, 2005, 102:4783-4788.
Facucho-Oliveira et al., "Mitochondrial DNA replication during differentiation of murine embryonic stem cells," J. Cell Sci., 2007, 120:4025-4034.
Folmes et al., "Somatic oxidative bioenergetics transitions into pluripotency-dependent glycolysis to facilitate nuclear reprogramming," Cell Metabolism, Aug. 2011, 14(2):264-271.

Friis et al., "A glycolytic burst drives glucose induction of global histone acetylation by picNuA4 and SAGA," Nucleic Acids Res., 2009, 37:3969-3980.
Govindaraju et al., "Proton NMR chemical shifts and coupling constants for brain metabolites," NMR Biomed., 2000, 13:129-153.
Hochedlinger and Plath, "Epigenetic reprogramming and induced pluripotency," Development, 2009, 136:509-523.
Huangfu et al., "Induction of pluripotent stem cells by defined factors is greatly improved by small-molecule compounds," Nat. Biotechnol., 2008, 26:795-797.
Jia et al., "A nonviral minicircle vector for deriving human iPS cells," Nat. Methods, 2010, 7(3):197-199.
Kim et al., "Generation of human induced pluripotent stem cells by direct delivery of reprogramming proteins," Cell Stem Cell, 2009, 4(6):472-476.
Ko et al., "Glucose catabolism in the rabbit VX2 tumor model for liver cancer: characterization and targeting hexokinase," Cancer Lett., 2001, 173:83-91.
Kondoh et al., "Glycolytic enzymes can modulate cellular life span," Cancer Res., 2005, 65:177-185.
Kondoh et al., "A high glycolytic flux supports the proliferative potential of murine embryonic stem cells," Antioxid. Redox. Signal., 2007, 9:293-299.
Kovacic et al., "Akt activity negatively regulates phosphorylation of AMP-activated protein kinase in the heart," J. Biol. Chem., 2003, 278:39422-39427.
Krizhanovsky and Lowe, "Stem cells: The promises and perils of p53," Nature, 2009, 460:1085-1086.
Kruger et al., "1H NMR metabolite fingerprinting and metabolomic analysis of perchloric acid extracts from plant tissues," Nat. Protoc., 2008, 3:1001-1012.
Kruse and Gu, "p53 aerobics: the major tumor suppressor fuels your workout," Cell Metab., 2006, 4:1-3.
Lin et al., "A chemical platform for improved induction of human iPSCs," Nat. Methods, 2009, 6(11):805-808.
Lomenick et al., "Target identification using drug affinity responsive target stability (DARTS)," Proc. Natl. Acad. Sci. USA, 2009, 106:21984-21989.
Lonergan et al., "Mitochondria in stem cells," Mitochondrion, 2007, 7:289-296.
Marion et al., "Telomeres acquire embryonic stem cell characteristics in induced pluripotent stem cells," Cell Stem Cell, 2009, 4:141-154.
Martinez-Ferandez et al., "c-MYC independent nuclear reprogramming favors cardiogenic potential of induced pluripotent stem cells," J Cardiovascular Translational Res., Feb. 2010, 3(1):1-16.
Martinez-Ferandez et al., "iPS programmed without c-MYC yield proficient cardiogenesis for functional heart chimerism," Circulation Res., Sep. 2009, 105(7):648-656.
Meissner et al., "Direct reprogramming of genetically unmodified fibroblasts into pluripotent stem cells," Nat. Biotechnol., 2007, 25:1177-1181.
Mikkelsen et al., "Dissecting direct reprogramming through integrative genomic analysis," Nature, 2008, 454:49-55.
Mueller et al., "An assessment of software solutions for the analysis of mass spectrometry based quantitative proteomics data," J. Proteome Res., 2008, 7:51-61.
Nelson et al., "Induced pluripotent reprogramming from promiscuous human stemness related factors," Clin. Transl. Sci., 2009, 2(2):118-26.
Nelson et al., "Induced pluripotent stem cells: developmental biology to regenerative medicine," Nat. Rev. Cardiol., 2010, 7(12):700-10.
Nelson et al., "Repair of acute myocardial infarction by human stemness factors induced pluripotent stem cells," Circulation, 2009, 120:408-416.
Neubert et al., "Label-free detection of differential protein expression by LC/MALDI mass spectrometry," J. Proteome Res., 2008, 7:2270-2279.
Okita et al., "Generation of mouse-induced pluripotent stem cells with plasmid vectors," Nat. Protoc., 2010, 5(3):418-28.
Panopoulos et al., "Anaerobicizing into Pluripotency," Cell Metabol., Aug. 2011, 14:143-144.

(56) References Cited

OTHER PUBLICATIONS

Passos et al., "Mitochondrial dysfunction accounts for the stochastic heterogeneity in telomere-dependent senescence," PLoS Biol., 2007, 5:e110, 14 pages.

Perez-Terzic et al., "Stem cells transform into a cardiac phenotype with remodeling of the nuclear transport machinery," Nat. Clin. Pract. Cardiovasc. Med., 2007, 4(Suppl 1):S68-76.

Prigione et al., "The senescence-related mitochondrial/oxidative stress pathway is repressed in human induced pluripotent stem cells," Stem Cells, 2010, 28:721-733.

Seagle et al., "High-throughput nuclear magnetic resonance metabolomic footprinting for tissue engineering," Tissue Eng. Part C Methods, 2008, 14(2):107-18.

Shao et al., "Calibration by NMR for quantitative analysis: p-toluenesulfonic acid as a reference substance," J. Chromatogr. A, 2007, 1138:305-308.

St John et al., "The expression of mitochondrial DNA transcription factors during early cardiomyocyte in vitro differentiation from human embryonic stem cells," Cloning Stem Cells, 2005, 7:141-153.

Stacpoole, "The pharmacology of dichloroacetate," Metabolism., 1989, 38:1124-1144.

Takahashi and Yamanaka, "Induction of pluripotent stem cells from mouse embryonic and adult fibroblast cultures by defined factors," Cell, 2006, 126:663-676.

Teperino et al., "Histone methyl transferases and demethylases; can they link metabolism and transcription?" Cell Metab., 2010, 12:321-327.

Turner et al., "Nuclear magnetic resonance metabolomic footprinting of human hepatic stem cells and hepatoblasts cultured in hyaluronan-matrix hydrogels," Stem Cells, 2008, 26:1547-1555.

Wellen et al., "ATP-citrate lyase links cellular metabolism to histone acetylation," Science, 2009, 324:1076-1080.

Wishart et al., "HMDB: a knowledgebase for the human metabolome," Nucleic Acids Res., 2009, 37:D603-610.

Yoshida et al., "Hypoxia enhances the generation of induced pluripotent stem cells," Cell Stem Cell, 2009, 5:237-241.

Zeuschner et al., "Induced pluripotent stem cells at nanoscale," Stem Cells Dev., 2010, 19:615-620.

Zhu et al., "Mass spectrometry-based label-free quantitative proteomics," J. Biomed. Biotechnol., 2010, Artile ID 840518, 7 pages.

Zhu et al., "Reprogramming of human primary somatic cells by OCT4 and chemical compounds," Cell Stem Cell, 2010, 7:651-655.

Zlatkovic et al., "Proteomic profiling of KATP channel-deficient hypertensive heart maps risk for maladaptive cardiomyopathic outcome," Proteomics, 2009, 9:1314-1325.

Zlatkovic-Lindor et al., "ATP-sensitive K(+) channel-deficient dilated cardiomyopathy proteome remodeled by embryonic stem cell therapy," Stem Cells, 2010, 28:1355-1367.

* cited by examiner

METHODS AND MATERIALS FOR OBTAINING INDUCED PLURIPOTENT STEM CELLS

CROSS REFERENCE TO RELATED APPLICATIONS

This application is a National Stage application under 35 U.S.C.§371 of International Application No. PCT/US2012/051751, having an International Filing Date of Aug. 21, 2012, which claims the benefit of U.S. Provisional Application Ser. No. 61/526,066, filed Aug. 22, 2011. The disclosure of the prior applications is considered part of (and is incorporated by reference in) the disclosure of this application.

STATEMENT AS TO FEDERALLY SPONSORED RESEARCH

This invention was made with government support under HL083439, HL085208, HL007111, and AI074363 awarded by National Institutes of Health. The government has certain rights in the invention.

BACKGROUND

1. Technical Field

This document relates to methods and materials involved in obtaining induced pluripotent stem (iPS) cells. For example, this document relates to methods and materials for increasing the efficiency of making iPS cells as well as methods and materials for selecting iPS cells.

2. Background Information

Coerced expression of stemness transcription factors can be used to reprogram somatic cell fate to achieve pluripotent capacity and to endow an embryonic-like propensity for multilineage differentiation, the hallmark of iPS cells (Takahashi and Yamanaka, *Cell,* 126:663-676 (2006); Meissner et al., *Nat. Biotechnol.,* 25:1177-1181 (2007); Mikkelsen et al., *Nature,* 454:49-55 (2008); Hochedlinger and Plath, *Development,* 136:509-523 (2009); and Nelson et al., *Nat. Rev. Cardiol.,* 7(12):700-10 (2010)). iPS cells as well as cells formed from iPS cells have many potential uses. For example, iPS cells and cells formed from iPS cells have the potential to allow clinicians to carry out cell therapies without using embryotic tissue. In some cases, iPS cells can be used to carry out patient-specific cell therapies. For example, iPS cells can be created from a patient sample and used to generate a population of differentiated cells for a desired treatment that can be administered to that same patient.

SUMMARY

This document provides methods and materials involved in obtaining iPS cells. For example, this document relates to methods and materials for increasing the efficiency of making iPS cells as well as methods and materials for selecting iPS cells. As described herein, the efficiency of producing iPS cells by the coerced expression of stemness transcription factors (e.g., OCT3/4, SOX2, and KLF4 with or without c-MYC) can be improved by exposing the cells to one or more ingredients (e.g., glucose) that promote or assist in glycolytic metabolism. For example, culturing somatic cells exposed to stemness transcription factors to induce pluripotent stem cell formation can be performed in the presence of between 5 mM and 25 mM of glucose (e.g., the presence of between 5 mM and 25 mM of exogenously added glucose). Such culturing can result in at least a 2.5 percent (e.g., at least a 5, 15, 20, 25, 30, 35, 40, 45, 50, 75, 100 percent) increase in iPS cell formation as compared to a comparable culturing procedure that lacks the presence of between 5 mM and 25 mM of glucose (e.g., lacks the presence of between 5 mM and 25 mM of exogenously added glucose). Increasing the efficiency of iPS cell formation can allow for the formation of more iPS cells in a shorter period of time. In some cases, increasing the efficiency of iPS cell formation can allow for the formation of a large number of different iPS cells that can be evaluated for a desired trait or set of traits.

As also described herein, markers of glycolytic metabolism (e.g., increased glycolytic metabolism) can be used to identify somatic cells being exposed to the coerced expression of stemness transcription factors that are likely to form iPS cells. In some cases, markers of increased glycolytic metabolism and increased mitochondrial membrane potential can be used to identify iPS cells within a culture of somatic cells being exposed to the coerced expression of stemness transcription factors. For example, stains such as tetramethylrhodamine methyl ester (TMRM) can be used to identify somatic cells (e.g., cells being exposed to the coerced expression of stemness transcription factors) that are likely to form iPS cells. In some cases, a culture of somatic cells being exposed to the coerced expression of stemness transcription factors can be treated with TMRM to stain those somatic cells that were reprogrammed into iPS cells. Having the ability to identify iPS cells based at least in part on an increased level of glycolysis can allow for the isolation of more iPS cells in a shorter period of time. In some cases, having the ability to identify iPS cells based at least in part on an increased level of glycolysis can allow for the isolation of a large number of different iPS cells that can be evaluated for a desired trait or set of traits.

In general, one aspect of this document features a method for augmenting production of induced pluripotent stem cells being produced from somatic cells by the expression of stemness transcription factors. The method comprises, or consists essentially of, contacting the somatic cells with an effective amount of an agent that promotes or aids glycolysis. The somatic cells can be fibroblasts. The stemness transcription factors can be OCT3/4, SOX2, KLF4, or c-MYC. The stemness transcription factors can be OCT3/4, SOX2, and KLF4. The agent can be glucose. The agent can be glucose, and the effective amount can be between 5 mM and 25 mM.

In another aspect, this document features a method for identifying induced pluripotent stem cells within a sample comprising a mixture of somatic cells and the induced pluripotent stem cells. The method comprises, or consists essentially of, (a) contacting the sample with a marker of glycolysis, wherein the marker labels the induced pluripotent stem cells to a greater extent than the somatic cells, and (b) obtaining the induced pluripotent stem cells from the mixture based at least in part on an increased level of the marker being associated with the induced pluripotent stem cells. The sample can be an in vitro culture sample. The somatic cells can be fibroblasts. The induced pluripotent stem cells can be cells that were produced from the somatic cells by the expression of stemness transcription factors. The stemness transcription factors can be OCT3/4, SOX2, KLF4, or c-MYC. The stemness transcription factors can be OCT3/4, SOX2, and KLF4. The induced pluripotent stem cells can be cells that were produced in the presence of an effective amount of an agent that promotes or aids glycolysis. The agent can be glucose. The agent can be glucose, and the effective amount can be between 5 mM and 25 mM. The marker can be lactate.

In another aspect, this document features a method for identifying induced pluripotent stem cells within a sample comprising a mixture of somatic cells and the induced pluripotent stem cells. The method comprises, or consists essentially of, (a) contacting the sample with a marker of mitochondrial membrane potential, wherein the marker labels the induced pluripotent stem cells to a greater extent than the somatic cells, and (b) obtaining the induced pluripotent stem cells from the mixture based at least in part on an increased level of the marker being associated with the induced pluripotent stem cells. The sample can be an in vitro culture sample. The somatic cells can be fibroblasts. The induced pluripotent stem cells can be cells that were produced from the somatic cells by the expression of stemness transcription factors. The stemness transcription factors can be OCT3/4, SOX2, KLF4, or c-MYC. The stemness transcription factors can be OCT3/4, SOX2, and KLF4. The induced pluripotent stem cells can be cells that were produced in the presence of an effective amount of an agent that promotes or aids glycolysis. The agent can be glucose. The agent can be glucose, and the effective amount can be between 5 mM and 25 mM. The marker can be tetramethylrhodamine methyl ester or 5,5',6,6'-tetrachloro-1,1',3,3'-tetraethyl-benzimidazolylcarbocyanine iodide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
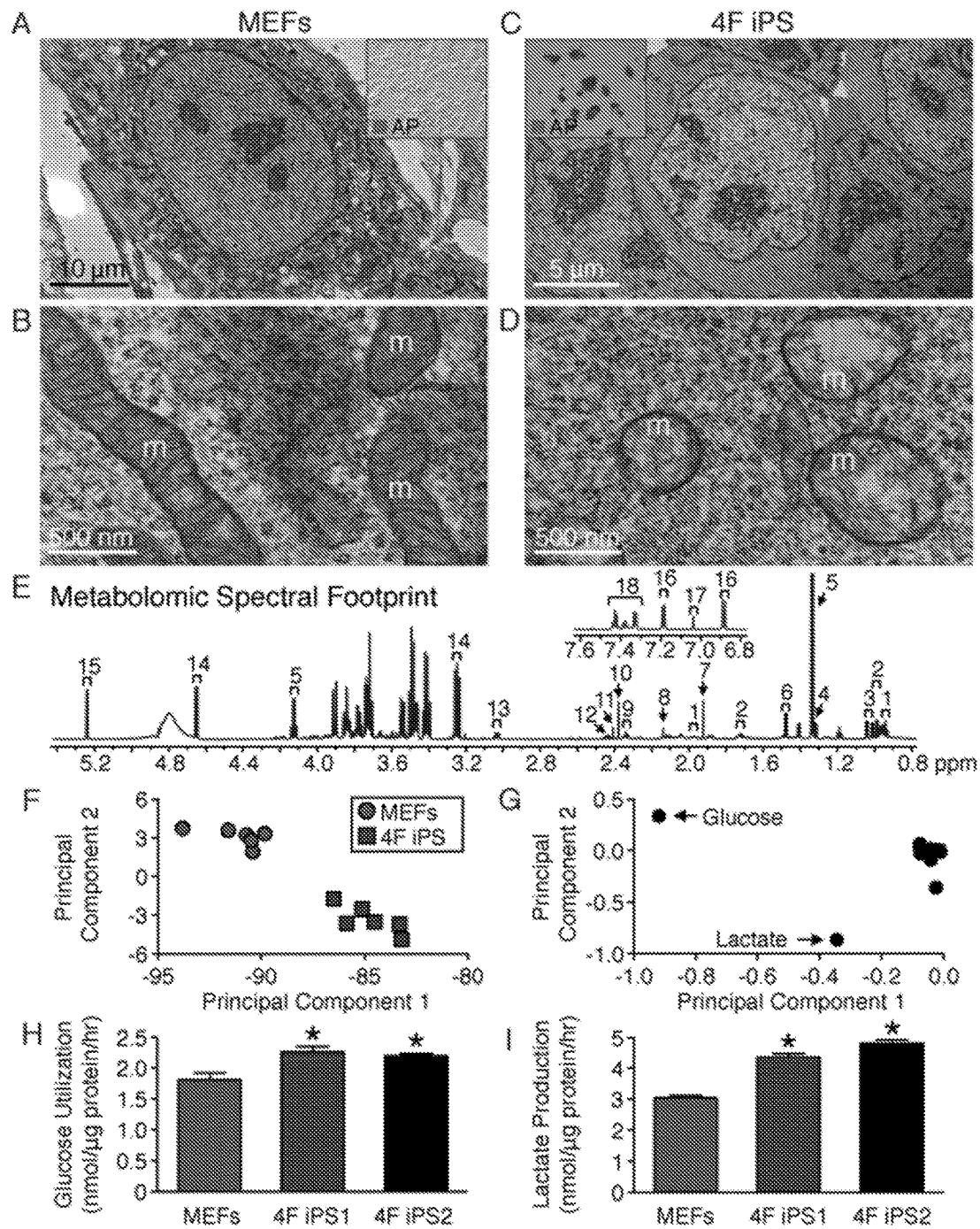
FIGS. 1A-I. Nuclear reprogramming transforms mitochondrial structure inducing a distinct metabolomic footprint. Nuclear reprogramming induced regression from mature elongated and cristae-rich mitochondria (m) of mouse embryonic fibroblasts (MEFs) (A, B) to immature spherical and cristae-poor remnant structures in four stemness factor derived iPS cells (4F iPS) (C, D). Representative $^1$H NMR spectra of extracellular metabolites from 4F iPS cells: 1—isoleucine, 2—leucine, 3—valine, 4—threonine, 5—lactate, 6—alanine, 7—acetate, 8—methionine, 9—glutamate, 10—pyruvate, 11—succinate, 12—glutamine, 13—lysine, 14—β-glucose, 15—α-glucose, 16—tyrosine, 17—histidine, and 18—phenylalanine (E). Principal component analysis segregated 4F iPS metabolomic phenotypes away from the MEF profile with principal component 1 accounting for 88.3% and component 2 accounting for 7.6% of the total variance (F). The loading plot assigned glucose and lactate as key metabolites contributing to segregation (G). The increased utilization of glucose and production of glycolytic end products in excess of parental MEFs (H, I) were reproduced in independent iPS lines (4F iPS1 and 4F iPS2). Values are mean±SEM, n=6. P<0.05 versus MEFs. See also FIG. 5.

This document provides methods and materials involved obtaining iPS cells. For example, this document provides methods and materials for increasing the efficiency for making and/or selecting iPS cells. As described herein, the efficiency of producing iPS cells by the coerced expression of stemness transcription factors (e.g., OCT3/4, SOX2, and KLF4 with or without c-MYC) can be improved by exposing the cells to one or more agents (e.g., glucose) that promote or aid in glycolytic metabolism.

Any appropriate method can be used as a baseline induction method for producing iPS cells. For example, vectors such as adenoviral or other viral vectors can be used to direct the expression of polypeptides (e.g., stemness transcription factors) capable of inducing iPS cell formation from somatic cells. Examples of such polypeptides include, without limitation, OCT3/4, SOX2, KLF4, c-MYC, Nanog, and LIN-28. In some cases, vectors designed to express OCT3/4, SOX2, and KLF4 and not c-MYC can be used to produce iPS cells.

Other appropriate methods for producing iPS cells from somatic cells include, without limitation, induction with plasmid and/or minicircle DNA, mRNA, proteins, and small molecules as described elsewhere (Takahashi and Yamanaka, *Cell*, 126:663-676 (2006); Meissner et al., *Nat. Biotechnol.*, 25:1177-1181 (2007); Mikkelsen et al., *Nature*, 454:49-55 (2008); and Nelson et al., *Nat. Rev. Cardiol.*, 7(12):700-10 (2010); Okita et al., *Nat. Protoc.*, 5(3):418-28 (2010); Jia et al., *Nat. Methods*, 7(3):197-199 (2010); Anokye-Danso et al., *Cell Stem Cell*, 8(4):376-88 (2011); Kim et al., *Cell Stem Cell*, 4(6):472-476 (2009); and Lin et al., *Nat. Methods*, 6(11):805-808 (2009)). In some cases, iPS cells can be produced using a baseline method such as those described elsewhere (Nelson et al., *Clin. Transl. Sci.*, 2(2): 118-26 (2009)).

As described herein, a baseline induction method can be augmented by including one or more agents that are capable of promoting or aiding in glycolytic metabolism. Examples of agents that are capable of promoting or aiding in glycolytic metabolism and can be used as described herein include, without limitation, glucose, fructose 2,6-bisphosphate, and glucose-6-phosphate. Any appropriate amount of an agent capable of promoting or aiding in glycolytic metabolism can be included. For example, when using glucose in a standard culturing setting, between about 5 mM and about 25 mM (e.g., between about 10 mM and about 25 mM, between about 15 mM and about 25 mM, between about 20 mM and about 25 mM, between about 5 mM and about 20 mM, or between about 5 mM and about 15 mM) of glucose can be added to the culture medium. In some cases, a combination of agents capable of promoting or aiding in glycolytic metabolism can be used to improve the efficiency of iPS cells formation of a baseline induction method.

In some cases, iPS cells can be produced by culturing somatic cells transfected with one or more adenoviral or other viral vectors constructed to express an OCT3/4, SOX2, and KLF4 with or without c-MYC in the presence of between about 5 mM and about 25 mM of an agent that promotes or aids in glycolytic metabolism (e.g., glucose). In some cases, to produce iPS cells, a method described in International Patent Application Publication No. WO 2010/017562 can be designed to include a culturing step whereby the cells are cultured in the presence of an agent that promotes or aids in glycolytic metabolism (e.g., glucose).

In some cases, the efficiency of producing iPS cells by the coerced expression of stemness transcription factors (e.g., OCT3/4, SOX2, and KLF4 with or without c-MYC) can be improved by exposing the cells to one or more agents that reduce or interfere with oxidative metabolism. For example, any appropriate method described herein or any appropriate baseline induction method can be augmented by including one or more agents that are capable of reducing or interfering with oxidative metabolism. Examples of agents that are capable of reducing or interfering with oxidative metabolism and can be used as described herein include, without limitation, 2,4-dinitrophenol, cyanide, carbon monoxide, azide, oligomycin, malonate, oxaloacetate, carbonyl cyanide m-chlorophenyl hydrazone (CCCP), and rotenone. Any appropriate amount of an agent capable of reducing or interfering with oxidative metabolism can be included. For example, when using a standard culturing setting, between about 75 µM and about 125 µM (e.g., about 100 µM) of 2,4-dinitrophenol can be added to the culture medium. In some cases, a combination of agents capable of reducing or interfering with oxidative metabolism can be used to improve the efficiency of iPS cells formation of a baseline induction method.

In some cases, iPS cells can be produced by culturing somatic cells transfected as described in International Patent Application Publication No. WO 2010/017562. Once the viruses are removed for those methods that include the use of viruses, an agent capable of reducing or interfering with oxidative metabolism (e.g., 2,4-dinitrophenol) can be added. The agent capable of reducing or interfering with oxidative metabolism can be maintained in the culture media during the complete reprogramming process. For example, media containing the agent capable of reducing or interfering with oxidative metabolism can be changed daily to include the agent during the complete reprogramming process.

In some cases, one or more agents that are capable of promoting or aiding in glycolytic metabolism can be used in combination with one or more agents capable of reducing or interfering with oxidative metabolism.

When compared to a comparable background induction method, a method provided herein can result in at least a 10 percent increase (e.g., 10, 25, 50, 75, 100, or more percent increase) in the total number of iPS cells produced. For example, culturing fibroblasts transfected with nucleic acid that drives expression of OCT3/4, SOX2, and KLF4 in the presence of about 12.5 mM of glucose can result in 30-fold more iPS cells as compared to a similar method in the presence of 0 mM of glucose.

This document also provides methods and materials for selecting iPS cells. As described herein, one or more markers of glycolytic metabolism (e.g., increased glycolytic metabolism) can be used to identify somatic cells being exposed to the coerced expression of stemness transcription factors that are likely to form iPS cells. In some cases, one or more markers of glycolytic metabolism can be used to identify iPS cells within a culture of somatic cells being exposed to the coerced expression of stemness transcription factors. Examples of markers of glycolytic metabolism include, without limitation, glucose utilization, lactate, and acetate.

In some cases, one or more markers of mitochondria membrane potential can be used to identify somatic cells being exposed to the coerced expression of stemness transcription factors that are likely to form iPS cells. For example, cells within a culture of somatic cells being exposed to the coerced expression of stemness transcription factors that are associated with an elevated marker of mitochondria membrane potential can be identified as being an iPS cell or a cell likely to form an iPS cell. Examples of markers of mitochondria membrane potential include, without limitation, tetramethylrhodamine methyl ester, JC-1 (5,5',6,6'-tetrachloro-1,1',3,3'-tetraethylbenzimidazolylcarbocyanine iodide), and red-fluorescent dyes such as MitoTracker® Red CMXRos.

Once a culture of somatic cells being exposed to the coerced expression of stemness transcription factors is evaluated for one or more markers of glycolytic metabolism, one or more markers of mitochondria membrane potential, or a combination thereof, cells determined to be developing more glycolytic metabolism as compared to oxidative metabolism or as having increased mitochondria membrane potential can be identified as being iPS cells or cells likely to form iPS cells. For example, iPS cells can be identified from a mixture of somatic cells and iPS cells based, at least in part, on the positive or elevated staining for a marker of glycolytic metabolism, on the positive or elevated staining for a marker of mitochondrial membrane potential, or both.

Any appropriate method can be used to detect the presence or absence of a particular marker. For example, visual inspection can be used when stains or fluorescent markers are used (e.g., fluorescently-labeled antibodies). In some cases, fluorescence-activated cell sorting can be used to obtain cells having a particular fluorescence pattern.

Once obtained, the iPS cells can be treated with a desired set of factors to promote the differentiation of the iPS into a desired cell type. Such cells can be implanted into a mammal (e.g., a human) to treat a particular condition.

The invention will be further described in the following examples, which do not limit the scope of the invention described in the claims.

EXAMPLES

Example 1

Metabolic Remodeling from Somatic Oxidative Bioenergetics to Pluripotency-Dependent Glycolysis Underlies Nuclear Reprogramming Transduction into iPS Cells Mouse embryonic fibroblasts (MEFs) were transduced with HIV-based viral vectors encoding OCT3/4, SOX2, and KLF4 either in the presence (4F) or absence of c-MYC (3F) to produce iPS clones that met pluripotent criteria including expression of stem cell markers, embryoid body differentiation, teratoma formation, diploid aggregation, and contribution to organogenesis (Martinez-Fernandez et al., *Circ. Res.*, 105:648-656 (2009); Nelson et al., *Clin. Transl. Sci.*, 2:118-126 (2009); and Nelson et al., *Circulation*, 120:408-416 (2009)). Alternatively, iPS cells were derived with a viPS (Open Biosystems) kit. iPS cells were induced and maintained in ES Cell qualified DMEM supplemented with 15% FBS, 25 mM glucose, 2 mM Glutamax (Invitrogen), and 1 mM sodium pyruvate. In reprogramming experiments, media was supplemented with 0.25 or 1.25 mM 2DG (Sigma), 100 µM BrPA (Sigma) or 5 mM DCA (Sigma). Reprogramming efficiency was quantified using an alkaline phosphatase staining kit (Stemgent) or FACS analysis of SSEA-1 expression (Millipore) on a LSR II flow cytometer.

Ultrastructure

Mitochondrial density and morphology was evaluated in 1% glutaraldehyde and 4% formaldehyde fixed cells, and examined as ultramicrotome sections on a JEOL 1200 EXII electron microscope (Perez-Terzic et al., *Nat. Clin. Pract. Cardiovasc. Med.*, 4(Suppl 1):568-76 (2007)).

Metabolomic Footprinting and Fingerprinting

For footprinting of extracellular metabolites, 540 µL of media collected following 24 hours of culture was added to 60 µL of $D_2O$ (Sigma) containing 5 mM sodium 3-(trimethylsilyl)propionate-2,2,3,3-d4 (TSP) (Sigma) for chemical shift reference and 81.84 mM formate (Sigma) for peak quantification reference as described elsewhere (Turner et al., *Stem Cells*, 26:1547-1555 (2008)). Briefly, MEFs, iPS cells, and R1ESC were maintained in DMEM containing 15% FBS, pyruvate, L-glutamine, nonessential amino acids, 2-mercaptoethanol, and LIF in 6 well plates at 37° C. in a humidified incubator with 95% air and 5% $CO_2$ (Martinez-Fernandez et al., *Circ Res.*, 25; 105(7):648-56 (2009)). For footprinting analysis, cells were washed with PBS and fresh medium added prior to serial medium sample collection at 4, 8, and 12 hours (Seagle et al., *Tissue Eng. Part C Methods*, 14(2):107-18 (2008)). The remaining conditioned medium was collected at 24 hours, and cells were scraped in lysis buffer containing 20 mM Tris-HCl (pH 7.4 at 4° C.), 50 mM NaCl, 50 mM NaF, 5 mM Na pyrophosphate, 0.25 M sucrose, 0.1% Triton X-100, mini complete protease inhibitor, phosphatase inhibitor mixture I and II to assess protein content (Kovacic et al., *J. Biol. Chem.*, 278:39422-39427 (2003)).

For intracellular metabolite fingerprinting, neutralized perchloric acid extracts were concentrated with a SpeedVac and suspended in 600 µL of 100 mM phosphate buffer (pH 7.0) in $D_2O$ (Sigma) containing 0.5 mM TSP as described elsewhere (Beckonert et al., *Nat. Protoc.*, 2:2692-2703 (2007)). Briefly, metabolism was quenched by snap freezing cells in 6% perchloric acid/0.5 mM EGTA (Kruger et al., *Nat. Protoc.*, 3:1001-1012 (2008)). Cells were scraped and lysed with the homogenates centrifuged (1500×g for 5 minutes) to separate precipitated proteins from extracts containing water-soluble metabolites, which were subsequently neutralized with 0.5 M $K_2CO_3$. All samples were filtered through Costar Spin-X filters and added to 5 mm NMR tubes (Wilmad Labglass). $^1H$ NMR spectra were acquired on a Bruker Ultrashield 700 MHz spectrometer using a zgpr water pre-saturation pulse with an 11160.7 Hz spectral width, 32,000 points, acquisition time of 1.4680 seconds, relaxation delay of 14 seconds and 64 scans. All spectra were processed with exponential line broadening to 0.3 Hz and zero filling to 65,000 points. Following Fourier transformation, spectra were autophased with metabonomic phase correction, baseline corrected using a Bernstein polynomial fit and referenced to the TSP peak (0.00 ppm) using MestReNova 5.3.2 (MestRelab Research). p-toluenesulfonic acid (Sigma) was utilized as a reference standard to calibrate the formate concentration for quantitative analysis (Shao et al., *J. Chromatogr. A*, 1138:305-308 (2007)). Identities of $^1H$ NMR spectra peaks were assigned by comparison to reference values for chemical shift and multiplicity, and confirmed by comparison to spectra of pure compounds in the Human Metabolome database (Govindaraju et al., NMR Biomed., 13:129-153 (2000) and Wishart et al., *Nucleic Acids Res.*, 37:D603-610 (2009)). For metabolomic footprinting, net fluxes of metabolites were calculated by subtracting normalized concentrations of metabolites in basal media from concentrations of metabolites in 24-hour conditioned media. All metabolite values are normalized to total protein content as determined by a Bio-rad protein assay using the microplate procedure.

Metabolites and Oxygen Consumption

Lactate efflux rate was assessed in extracellular media using a using a lactate assay kit (SUNY at Buffalo, catalog no. A-108). Nucleotide concentrations were determined in neutralized perchloric acid extracts by high performance liquid chromatography, using a 0.1 M phosphate (pH 6.5), 0.01 M tetrabutylammoniumhydrogensulfate, and 40% methanol elution buffer (Chung et al., *Nat. Clin. Pract. Cardiovasc. Med.*, 4(Suppl 1):S60-67 (2007)). Oxygen consumption was assessed using an Oxygraph electrode system (Hansatech) on 5 million trypsinized cells suspended in DMEM. Maximal rate of uncoupled oxygen consumption was assessed by serial additions of 2,4-dinitrophenol (Sigma).

TMRM Fluorescence, Cell Sorting, and Gene Expression

Mitochondrial membrane potential was assessed daily (day 4-14) in reprogramming cells by incubating with 20 nM TMRM (Anaspec) for 30 minutes at 37° C. and imaged with a LSM 510 Axiovert laser confocal microscope. Following 1- and 2-weeks of reprogramming, single cell suspensions were incubated in TMRM and separated into two groups by a FACS Aria Cell Sorter; one consisting of the highest 10% of the population and the second consisting of the remaining live cells. Glycolytic and pluripotent gene expression of these population were examined on an Eco RT-PCR system (Illumina).

Mitochondrial membrane potential was assessed in live cells by staining with 1 μg/mL JC-1 (Invitrogen) for 30 minutes at 37° C. and quantified by FACS analysis on a LSR II flow cytometer. Alternatively, cells were incubated with 500 nM MitoTracker Red CMXRos (Invitrogen) for 30 minutes at 37° C., immunostained with anti-SSEA1 antibody (Millipore) and secondary goat anti-mouse IgG Alex Fluor 488, and nuclear stained with 4,6-diamidino-2-phenylindole (DAPI, Invitrogen). Images were acquired with a LSM 510 Axiovert laser confocal microscope.

Proteomics

Protein extracts were resolved by 2-D gel electrophoresis (2-DE) and 4-15% SDS-PAGE (100 and 30 mg, respectively) and silver stained (Arrell et al., J. Proteome Res., 8:4823-4834 (2009)). For comparative analysis, entire SDS-PAGE lanes were excised, destained, and prepared for LC-MS/MS, as were significantly altered protein species from 2-D gels identified by PDQuest analysis (Zlatkovic-Lindor et al., Stem Cells, 28:1355-1367 (2010)). Isolated tryptic peptides were analyzed and identified by LTQ-Orbitrap mass spectrometry. Label-free quantitative comparison of SDS-PAGE protein and peptide abundance was carried out on MS spectra using Rosetta Elucidator's differential workflow, with annotation performed using PeptideTeller and ProteinTeller (Neubert et al., J. Proteome Res., 7:2270-2279 (2008) and Lomenick et al., Proc. Natl. Acad. Sci. USA, 106:21984-21989 (2009)). Briefly, MEFs, iPS cells, and ESC were expanded to 80% confluency (10 cm dishes, n=4 per group). Cells were then washed extensively (ten 10 mL washes/plate) with PBS to remove extracellular protein, and following final PBS wash removal, protein was extracted by direct solubilization of adherent cells with 500 mL lysis buffer (7 M urea, 2 M thiourea, 2% [w/v] CHAPS), enabling protein separation by both two-dimensional (2-D) gel electrophoresis and SDS-PAGE. Protein was quantified in triplicate by a Bio-Rad protein assay using the microassay procedure with a bovine γ-globulin standard (Arrell et al., Clin. Pharmacol. Ther., 82:316-310 (2007); Arrell et al., Stem Cells, 26:387-400 (2008); and Arrell et al., J. Proteome Res., 8:4823-4834 (2009)). Protein resolution was carried out by 2-D gel electrophoresis (100 μg protein/gel, n=3 per experimental group) and 4-15% SDS-PAGE (30 μg protein/lane, n=4 per experimental group) prior to silver staining (Zlatkovic et al., Proteomics, 9:1314-1325 (2009)). Significantly altered protein species (Student's t-test, $P<0.05$) established by PDQuest analysis of 2-D gels were excised, destained, and prepared for LC-MS/MS, with isolated tryptic peptides identified following LTQ-Orbitrap mass spectrometry.

For label-free quantitative comparison of SDS-PAGE resolved samples, individual gel lanes were cut into 8 tranches, with each tranche reduced to 1 mm$^3$ pieces prior to destaining, in-gel trypsinolysis and peptide extraction, after which isolated peptides were analyzed and identified by LTQ-Orbitrap mass spectrometry. Using Rosetta Elucidator's multidimensional LC differential workflow, mass and retention time aligned mass spectral features were combined from the 8 tranches representing each sample, with feature annotation of sample composites performed using PeptideTeller and ProteinTeller to enable relative peptide and protein quantitation from identified spectral features (Mueller et al., J. Proteome Res., 7:51-61 (2008); and Zhu et al., J. Biomed. Biotechnol., 2010:840518 (2010). Data were analyzed statistically by three group one-way ANOVA with significance $P<0.05$ and fold-change $>1.5$ both required for proteins considered differentially expressed. Visual scripts were designed within Elucidator to extract unsupervised agglomerative clustering heatmaps that represent glycolytic and oxidative phosphorylation protein reorganization arising from nuclear reprogramming.

Statistical Analysis

Data are presented as mean±SEM. Metabolic footprinting and fingerprinting were analyzed using principle component analysis and JMP. Student t-test was used to evaluate two group comparisons, and ANOVA with a Bonferroni post-hoc correction was used for three group comparisons. A value of $P<0.05$ was considered significant.

Results

Figure 2:
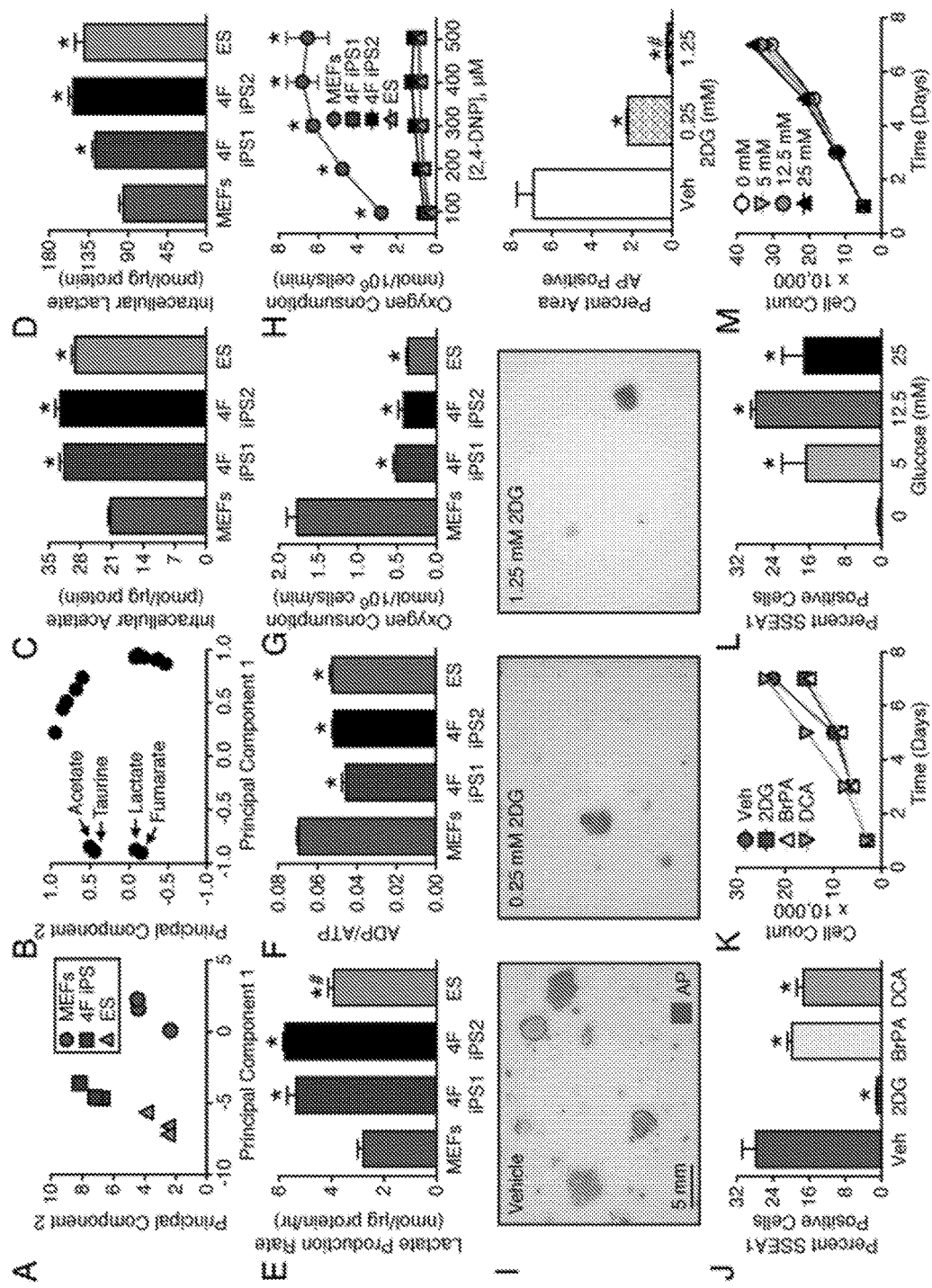
FIGS. 2A-M. Induction of pluripotency requires functional glycolysis. $^1$H NMR fingerprinting of intracellular metabolites segregated 4F iPS cells away from parental MEFs and towards ES cells (A). First principal component accounts for 66.7%, and the second principal component accounts for 24.7% of the total variance. Acetate, taurine, lactate, and fumarate were identified as differentiating metabolites (B). Intracellular concentrations of glycolytic end products were distinct in 4F iPS cells compared to MEFs, and were similar to ES patterns (C, D). Nuclear reprogramming elevated lactate efflux rates (E) and reduced energy turnover in 4F iPS cells, similar to that of ES cells (F). Compared to MEFs, iPS and ES had reduced basal oxygen consumption (G) and lower maximal uncoupled oxidative capacity (H). During reprogramming the glycolytic inhibitor, 2-deoxyglucose (2-DG), blunted induction of the pluripotency marker alkaline phosphatase (I). Glycolytic inhibitors, 1.25 mM 2-DG and 100 μM 3-bromopyruvic acid (BrPA) and alternatively a stimulator of oxidative pyruvate disposal, 5 mM dichloroacetate (DCA), reduced the proportion of reprogrammed cells, as assessed by SSEA-1 FACS analysis (J), without inducing a significant change in growth of the parental MEF population (K). Stimulation of glycolysis by elevating extracellular glucose promoted the number of cells achieving the reprogrammed state (L) without altering the growth of the MEF population (M). Values are mean±SEM, n=3 except for lactate efflux where n=6. In all panels except H, *P<0.05 versus MEFs and #P<0.05 versus 4F iPS cells. In H, *P<0.05 versus 4F iPS and ES cells. See also FIG. 6.

Nuclear Reprogramming Transforms Mitochondrial Infrastructure and the Metabolomic Footprint Four stemness transcription factor (4F) reprogramming restructured mouse embryonic fibroblasts (MEFs), characterized by organized mitochondrial networks, to a more primitive cytotype featuring an increased nuclear-to-cytosol ratio with few perinuclear mitochondria (FIG. 1, A-D). Mature tubular and cristae-rich somatic mitochondria transitioned into immature spherical and cristae-poor remnant structures in 4F iPS cells, suggesting bioenergetic remodeling (FIGS. 1, B and D). Metabolome-wide high-resolution $^1$H NMR decoded metabolic consequences of dedifferentiation (FIGS. 1, E and 5). Data reduction with principal component analysis separated the 4F iPS extracellular metabolite footprint away from the parental MEF landscape (FIG. 1, F) based on distinguishing metabolites, glucose and lactate (FIG. 1, G). Rates of glucose utilization (2.3±0.1 and 2.2±0.1 nmol/μg protein/hour) and lactate production (4.4±0.1 and 4.8±0.1 nmol/μg protein/hour) were significantly elevated in two 4F iPS lines (4F iPS1 and 4F iPS2) compared to MEFs (1.8±0.1 and 3.1±0.1 nmol/μg protein/hour, respectively, n=6, p<0.05; FIGS. 2, H and I). Thus, nuclear reprogramming induced mitochondrial regression and gave rise to an extracellular metabolome indicative of ongoing glucose consumption.

Metabolic Remodeling from Oxidative Metabolism to Functional Glycolysis is Required for Nuclear Reprogramming Intracellular metabolite fingerprinting validated the glycolytic capacity of 4F iPS cells, segregating the acquired metabolomic pattern away from parental MEFs and closer to the pluripotent ES cell standard (FIGS. 2, A and 5, B-C). Intracellular acetate and lactate distinguished the iPS metabolite pattern (FIG. 2, B). 4F iPS accumulation of acetate was similar to ES cells (31.6±0.9, 32.5±1.0 and 29.2±0.7 pmol/μg protein, n=3), and distinct from MEFs (21.3±0.5 pmol/μg protein, n=3 populations, p<0.05, FIG. 2, C). Comparably, lactate was equivalent in 4F iPS and ES groups (127±3, 152±5, and 140±10 pmol/μg protein, n=3), yet significantly different from MEFs (95±5 pmol/μg protein, n=3, p<0.05; FIG. 2, D). Lactate efflux (5.3±0.3 and 5.8±0.1 nmol/μg protein/hour) at a rate double that of MEFs (2.8±0.2 nmol/μg protein/hour, n=6, p<0.05; FIG. 2, E), indicated functional glycolysis in 4F iPS cells. Consistent with the lower efficiency of glycolytic ATP production compared to oxidative phosphorylation, the ADP/ATP ratio, an index of cellular energy turnover, was reduced in 4F iPS and ES cells (0.064±0.001, 0.052±0.001, and 0.057±0.002 versus 0.082±0.001 (MEFs), n=3, p<0.05, FIG. 2, F). In fact, oxygen consumption was low in 4F iPS and ES cells, compared to MEFs both at baseline (0.51±0.04, 0.42±0.07, and 0.36±0.02 versus 1.8±0.13 nmol/10$^6$ cells/minute, n=3, p<0.05, FIG. 2, G) and under electron transport chain uncoupling (0.98±0.10, 1.22±0.09, and 0.95±0.13 versus 6.51 ±1.05 nmol/10⁶ cells/min, n=3, p<0.05, FIG. 2, H). 4F iPS cells preserved the ability to generate mitochondrial membrane potential and demonstrated mitochondrial hyperpolarization (FIG. 7, A-C), a potential consequence of reduced ATP utilization.

Figure 6:
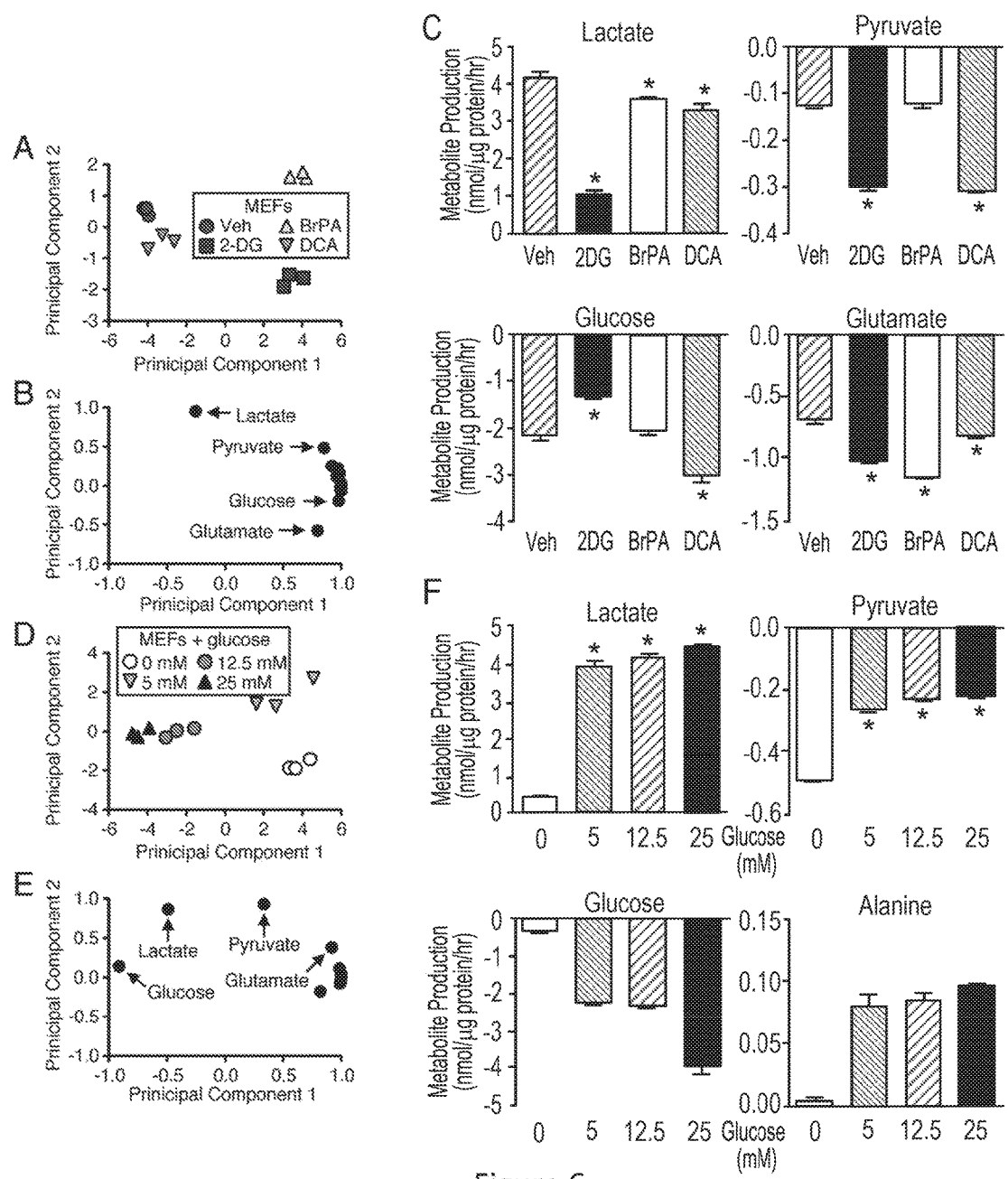
FIGS. 6A-F. Impact of metabolic modulators and glucose concentrations on parental MEFs. Principal component analysis segregated the $^1$H NMR cellular metabolomic footprints of MEFs treated 2DG, BrPA, and DCA from the vehicle (Veh) treated group (first principal component accounts for 88% and the second for 10% of the total variance) (A). The glycolytic metabolites lactate, pyruvate and glucose, as well as the oxidative metabolite glutamate, were components responsible for observed segregation (B). Treatment with 1.25 mM 2-deoxyglucose (2DG) reduced glucose utilization and lactate production, with greater utilization of glutamate and pyruvate, while 100 µM 3-bromopyruvic acid (BrPA) inhibited lactate production and accelerated glutamate utilization, consistent with inhibition of glycolysis and stimulation of oxidative metabolism (C). Dichloroacetate (DCA) treatment (5 mM) accelerated consumption of oxidative substrates (glucose, glutamate, and pyruvate) with modest impairment of lactate production, resulting in increased mitochondrial oxidative capacity (C). Principal component analysis also segregated metabolomic footprints of MEFs treated with different extracellular glucose concentrations (first principal component accounts for 85% and the second for 12% of the total variance) (D) and identified lactate, pyruvate, glucose, and alanine as metabolites contributing to the decoded pattern (E). With increased glucose availability, metabolomic footprinting demonstrated accelerated glucose utilization, alanine and lactate production and suppression of pyruvate utilization, consistent with reduced mitochondrial function (F). Of note, media supplemented with glutamate and pyruvate was sufficient to support growth of parental fibroblasts, suggesting that supplemented glucose may be preferentially utilized for anabolic processes during reprogramming. Values are mean±SEM, n=3. * P<0.05 versus vehicle in C and 0 mM glucose in (F).

Treatment of MEFs undergoing nuclear reprogramming with 2-deoxyglucose (2-DG), an inhibitor of glycolytic flux, blunted induction of the pluripotent marker alkaline phosphatase (FIG. 3, G), implicating a glycolytic requirement for iPS generation. Beyond 2-DG, a general inhibitor of glycolysis, the hexokinase 2 inhibitor 3-bromopyruvic acid (BrPA) (Ko et al., *Cancer Lett.*, 173:83-91 (2001)) and pyruvate dehydrogenase kinase (PDHK) inhibitor dichloroacetate (DCA) (Stacpoole, *Metabolism*, 38:1124-1144 (1989)) reduced reprogramming efficiency (0.9±0.3, 19.8±1.0, 17.3±1.5 versus 27.8±3.1% SSEA1 positive cells, n=3, p<0.05, FIG. 2, J) without impairing cell growth (FIG. 2, K). In control experiments, extracellular metabolite profiles of MEFs treated with 2-DG or BrPA were consistent with inhibition of glycolysis and stimulation of oxidative metabolism, while DCA treatment stimulated mitochondrial function and accelerated consumption of oxidative substrates (FIG. 6, A-C). Augmented glucose supplementation to stimulate glycolytic flux and reduce mitochondrial function (FIG. 6, D-F), increased SSEA1 positive cell generation (0.5±0.3 (0 mM glucose), 16.6±5.3 (5 mM), 27.8±1.1 (12.5 mM), and 17.1±4.7 (25 mM) % SSEA1 positive cells, n=3, p<0.05). Conversely, few MEFs underwent nuclear reprogramming in the absence of glucose (FIG. 2, L-M). Thus, conditions that favor glycolytic flux support, while conditions that favor oxidative energy metabolism impair, nuclear reprogramming.

Glycolytic Flux Fuels Induction of Pluripotency

Figure 3:
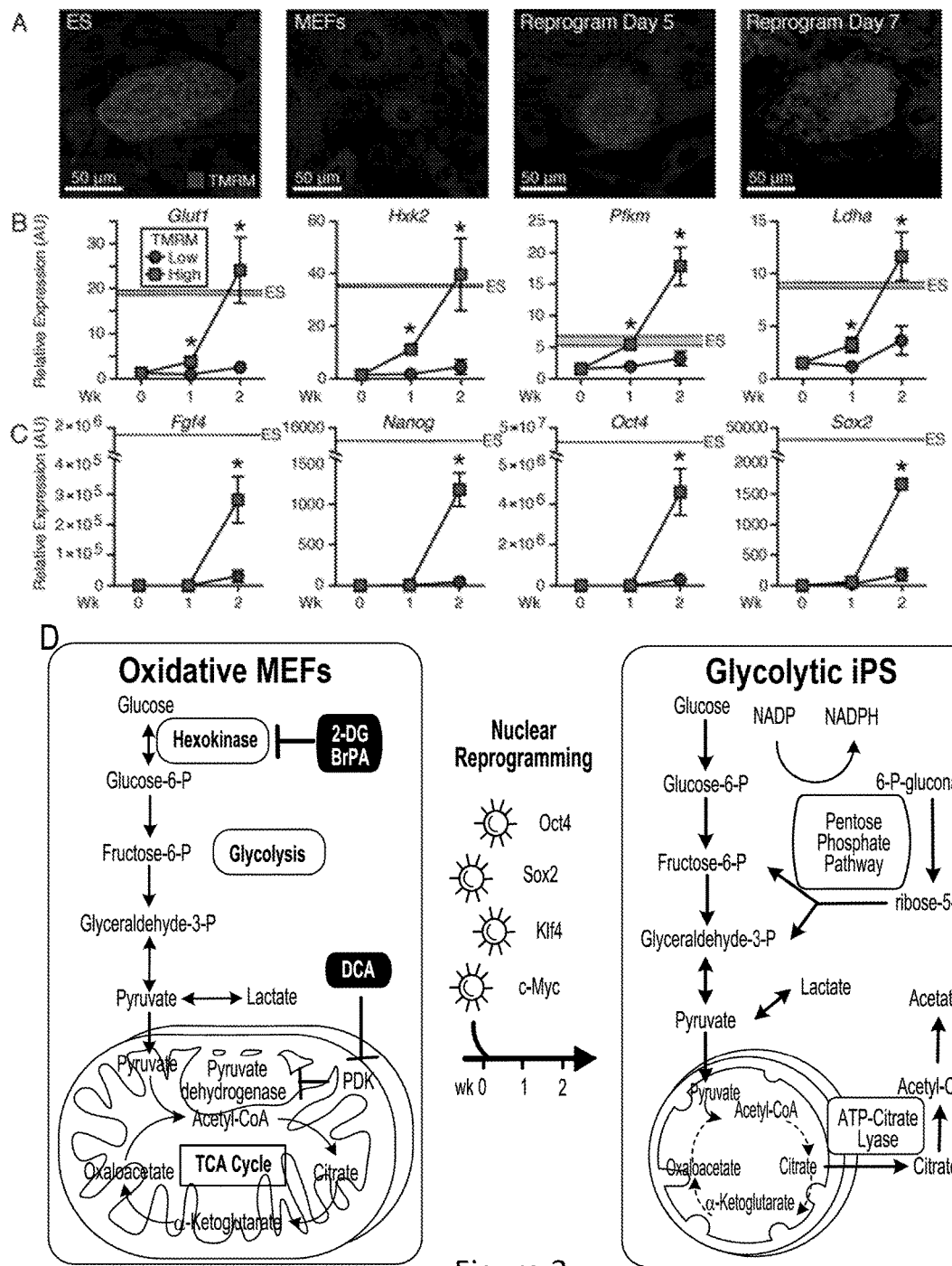
FIGS. 3A-D. Glycolytic engagement mobilizes pluripotent gene induction. Similar to ES cells and distinct from parental MEFs, live cell imaging of mitochondrial membrane potential identified nascent compact cell clusters with high tetramethylrhodamine methyl ester (TMRM) fluorescence within 5-7 days of nuclear reprogramming (A). Compared to the low/medium TMRM fluorescence population, the high TMRM fluorescence cells had significantly elevated glycolytic gene expression (Glut1, Hxk2, Pfkm, and Ldha) within 1-week of reprogramming, which met or exceeded ES cell glycolytic gene expression by 2-weeks of reprogramming (B). Of note, at 1-week of reprogramming pluripotent gene expression (Fgf4, Nanog, Oct4, and Sox2) remained low in the high TMRM fluorescence cells, similar to the starting MEFs, with pluripotent gene induction apparent during the second week (C). Shaded region represents mean±SEM for ES gene expression. Values are mean±SEM, n=3. * P<0.05 versus corresponding Low/Medium TMRM population. Nuclear reprogramming switches oxidative MEFs into glycolytic iPS cells (D). See also FIG. 7.
Figure 7:
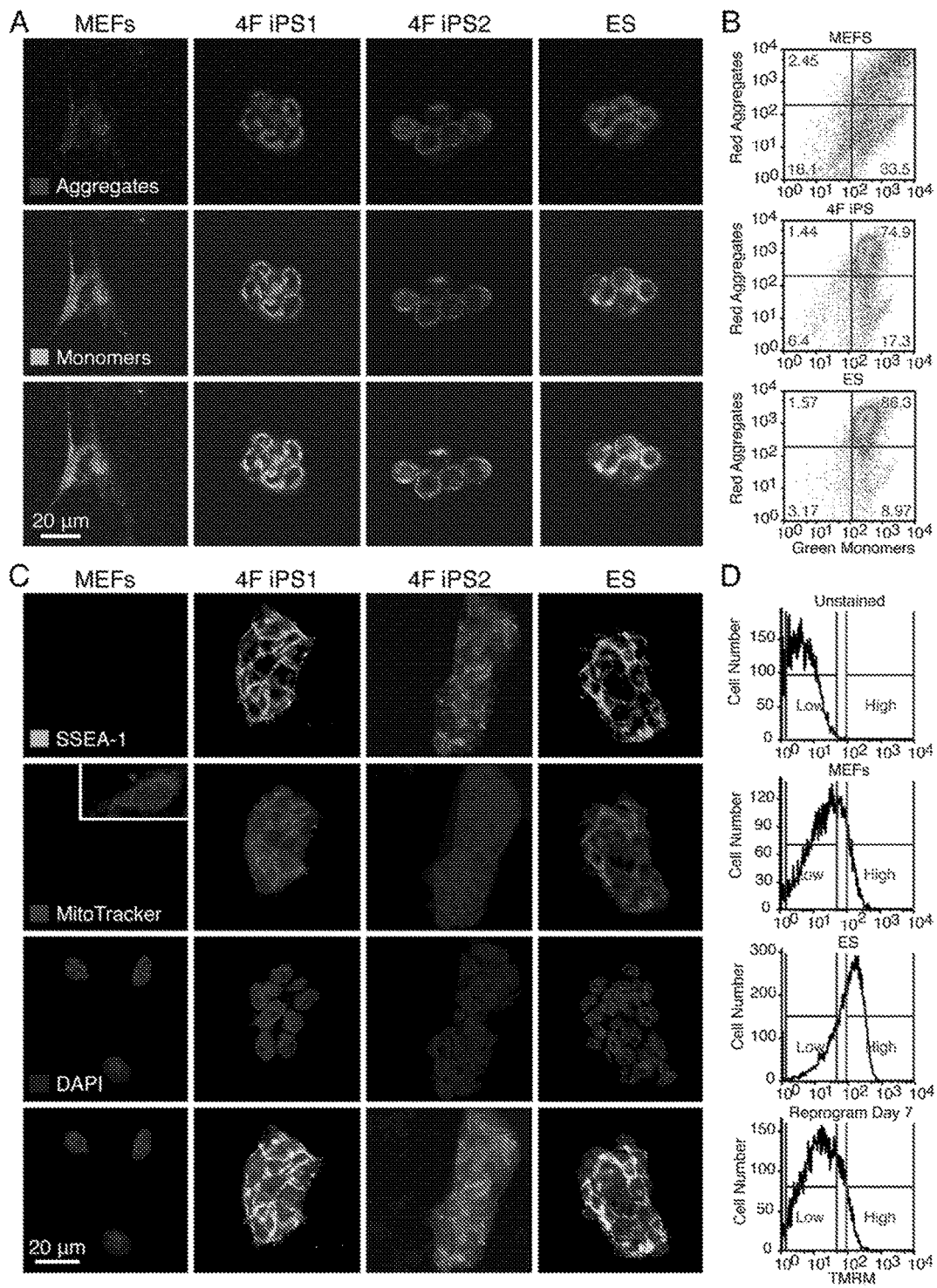
FIGS. 7A-D. Pluripotent cells demonstrate elevated mitochondrial membrane potential. Live cell staining indicated that iPS cells and ESC accumulated the potentiometric JC-1 dye as aggregates and monomers (A). Mitochondrial hyperpolarization was quantified using FACS analysis indicating a greater proportion of red aggregates in pluripotent cells compared to MEFs (B). MitoTracker Red CMXROS staining co-localized with expression of the pluripotent marker, SSEA1 (C). DAPI was utilized to counterstain nuclei. Inset demonstrates accumulation of MitoTracker Red, albeit at lower levels than in pluripotent cytotypes. Following two weeks of nuclear reprogramming cells were separated by FACS into a high TMRM fluorescence group consisting of compact cell clusters similar to ESC and a low TMRM group consisting of transfected but non-reprogrammed cells (D). Unstained represents a reprogramming population that was not incubated with TMRM prior to cell sorting. N=3 for each cell type.

Live cell imaging with the mitochondrial membrane potential sensitive probe, TMRM, revealed ES-like compact cell clusters with high fluorescence, compared to a low basal TMRM fluorescence in transduced yet non-established cells (FIG. 3, A). Temporal FACS sampling of high TMRM cells selected a population undergoing reprogramming, consistent with marked differences in mitochondrial membrane potential in parental MEFs versus derived iPS (FIG. 7, A-D). Compared to transduced but non-established cells with low TMRM fluorescence, reprogramming cells had significantly elevated glycolytic gene expression (Glut1, Hxk2, Pfkm, and Ldha) within 1-week of reprogramming, which met or exceeded by 2-weeks ES cell glycolytic gene expression (FIG. 3, B). In contrast, at 1-week of reprogramming pluripotent gene expression (Fgf4, Nanog, Oct4, and Sox2) remained low in the high TMRM cells, similar to the starting MEFs, with pluripotent gene induction apparent only after 2-weeks (FIG. 3, D). Therefore, the metabolic switch is not a mere feature of 4-factor transduction, but a biomarker of successful nuclear reprogramming, implicating that metabolic reprogramming fosters pluripotent gene expression induction (FIG. 3, E).

Figure 9:
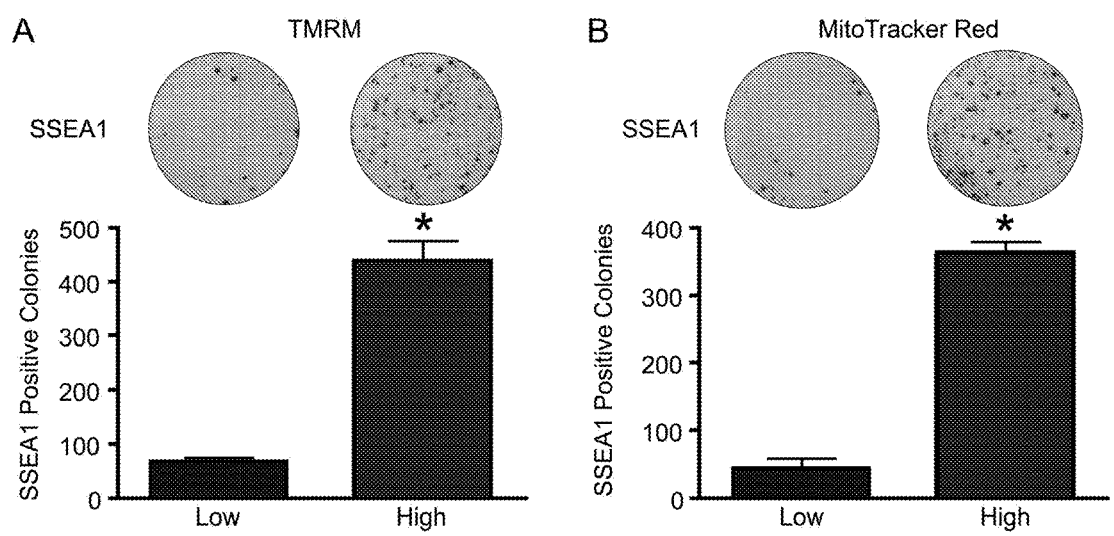
FIGS. 9A-B. Mitochondrial membrane potential selects reprogramming cells with greater propensity for iPS clone formation. Two weeks following reprogramming factor induction, cells were sorted by FACs into subpopulations with low and high mitochondrial membrane potential and were replated on inactive fibroblasts. Stem cell marker expression was assessed after an additional two weeks of cell culture, indicating that cells selected by high TMRM (A) or MitoTracker Red (B) fluorescence produced greater numbers of SSEA-1 positive colonies. P<0.05 versus low group.

In addition, mitochondrial membrane potential selected reprogramming cells with greater propensity for iPS clone formation (FIG. 9).

Reprogramming-Induced Metabolic Remodeling is Independent of c-Myc Induction

Figure 4:
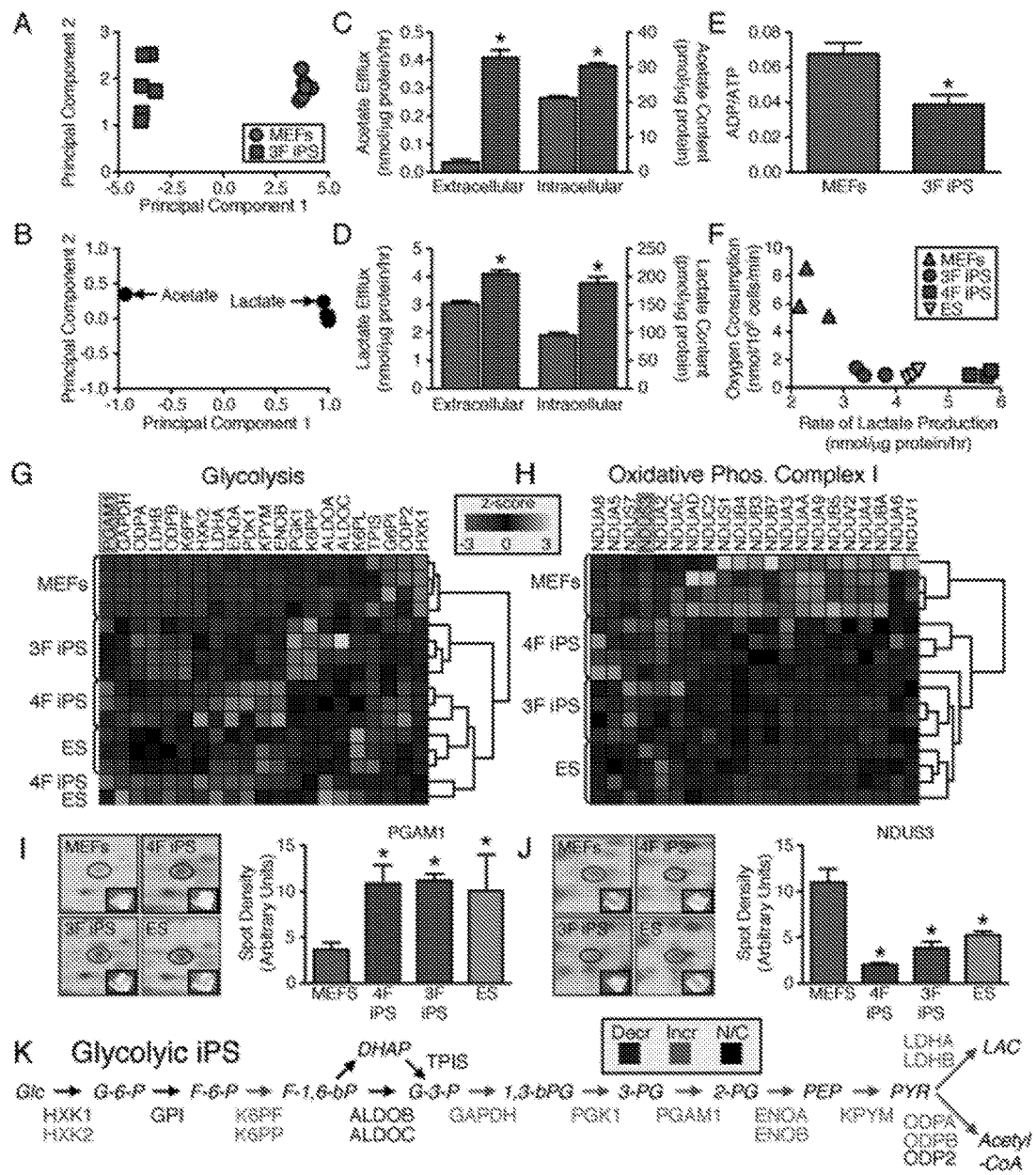
FIGS. 4A-K. Metabolic reprogramming is independent of c-Myc and is supported by selective metaboproteome remodeling. $^1$H NMR cellular metabolomic fingerprints (n=6) of three stemness factor induced iPS (3F IPS) segregated the 3F IPS pattern away from parental MEFs (first principal component accounts for 96.7%, and the second component accounts for 1.2% of the total variance) (A). Glycolytic end products, acetate and lactate, were key metabolites responsible for segregation (B). Intracellular content and efflux of acetate and lactate were significantly elevated in the 3F iPS compared to MEFs (C and D) and associated with reduced energy turnover (n=6) (E). Compared to MEFs, 3F iPS cells had lower maximal oxidative capacity and higher lactate production similar to that of ES cells, albeit not fully overlapping with 4F iPS (n=3) (F). Proteome-wide label-free quantification segregated iPS cells away from MEFs towards ES patterns based on agglomerative clustering of z-score transformed data (n=4), due to predominant glycolytic enzyme upregulation (G). Electron transport chain complex I subunits were predominantly downregulated in pluripotent cytotypes, which clustered away from MEFs (H). Examples of 2-DE quantification and MS/MS identification (n=3) independently confirms glycolytic upregulation (I) and complex I downregulation (J). iPS cell proteomic upregulation was mapped across the glycolytic pathway (K). Values are mean ±SEM. *P<0.05 versus MEFs. Proteins are abbreviated by Swiss-Prot gene name. See also FIG. 8 and Table 1.
Figure 5:
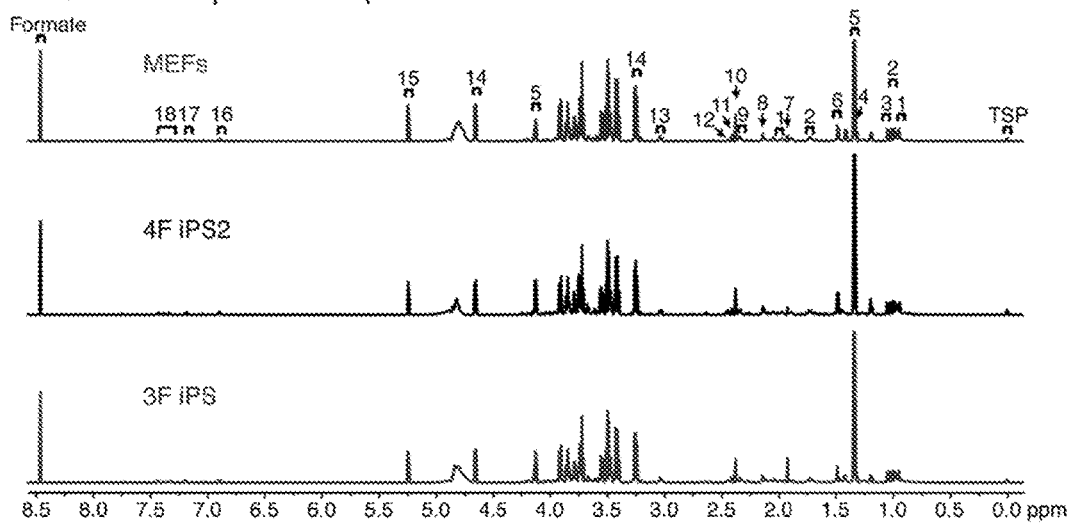
FIGS. 5A-C. Comparative $^1$H NMR metabolomic footprints and fingerprints from MEFS, iPS cells, and ESC. Metabolite peaks were identified as: 1—isoleucine, 2—leucine, 3—valine, 4—threonine, 5—lactate, 6—alanine, 7—acetate, 8—methionine, 9—glutamate, 10—pyruvate, 11—succinate, 12—glutamine, 13—lysine, 14—β-glucose, 15—α-glucose, 16—tyrosine, 17—histidine, 19—cysteine, 18—phenylalanine, 20—taurine, 21—glycine, 22—creatine, 23—phosphocreatine, and 24—ATP in representative metabolomic footprinting (A) and fingerprinting spectra (B). Principal components analysis identified intracellular concentrations of a representative amino acid, and tricarboxylic acid cycle intermediate were significantly modified in iPS cells compared to MEFs and were similar to ESC patterns. Values are mean±SEM, n=3. * P<0.05 versus MEFs. Metabolic production was assessed for the indicated cells and conditions (C)
Figure 5:
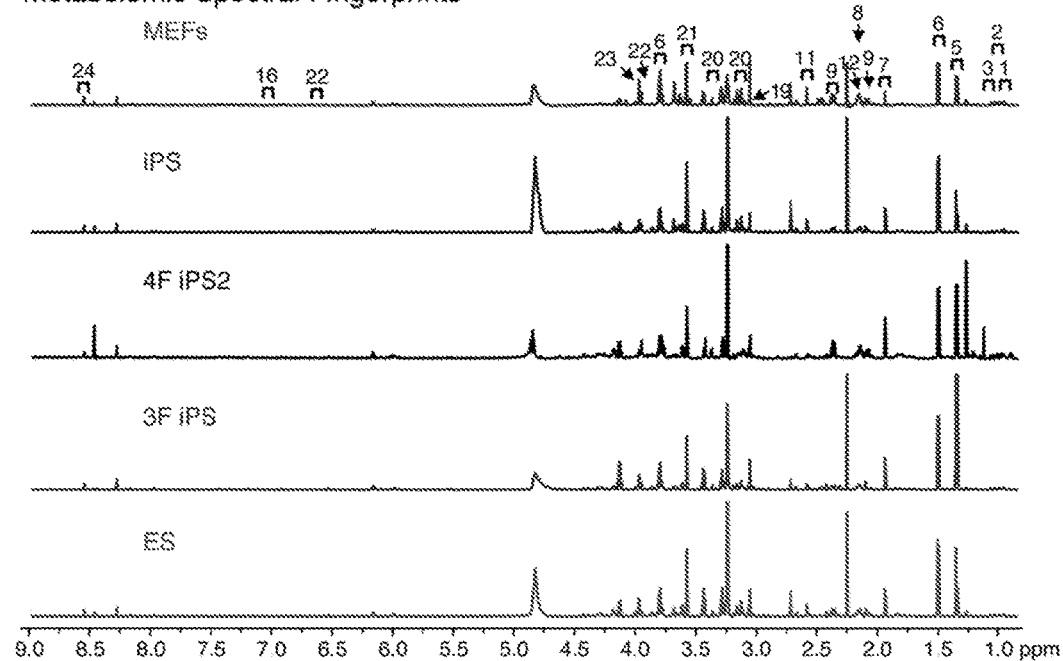
Figure 5:
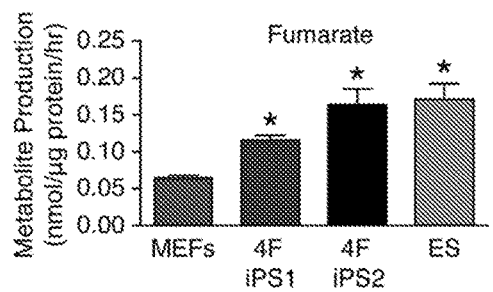
Figure 5:
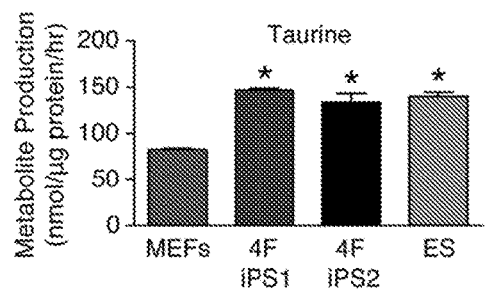

As c-Myc gene targets control rates of glycolysis and mitochondrial biogenesis (Dang, *Ernst Schering Found. Symp. Proc.*, pp. 35-53. (2007)), an additional cell line was derived without c-Myc (3F iPS). Similar to 4F iPS, ¹NMR metabolomic footprinting and fingerprinting segregated 3F iPS away from parental MEFs (FIG. 4, A-B), based upon the greater intracellular and extracellular accumulation of the glycolytic end products, acetate (intracellular: 30.4±0.8 versus 21.3±0.5 pmol/μg protein; extracellular: 0.41±0.03 versus 0.035±0.001 nmol/μg protein/hour, n=3, p<0.05, FIG. 4, C) and lactate (intracellular: 188±11 versus 95±5 pmol/μg protein; extracellular: 4.1±0.1 versus 3.0±0.1 nmol/μg protein/hour n=3, FIG. 4, D). Consistent with accelerated glycolysis, 3F iPS displayed reduced energy turnover compared to MEFs (0.039±0.005 versus 0.068±0.006, n=3, p<0.05, FIG. 4, E). In fact, 3F like 4F derived iPS demonstrated limited oxidative capacity and elevated lactate production compared to MEFs (FIG. 4, F). Thus, the nuclear reprogramming-induced metabolic switch from oxidative metabolism to glycolysis is independent of c-Myc induction and is a hallmark of bona fide iPS cells.

iPS Metabotype Arises Through Proteome Restructuring

Figure 8:
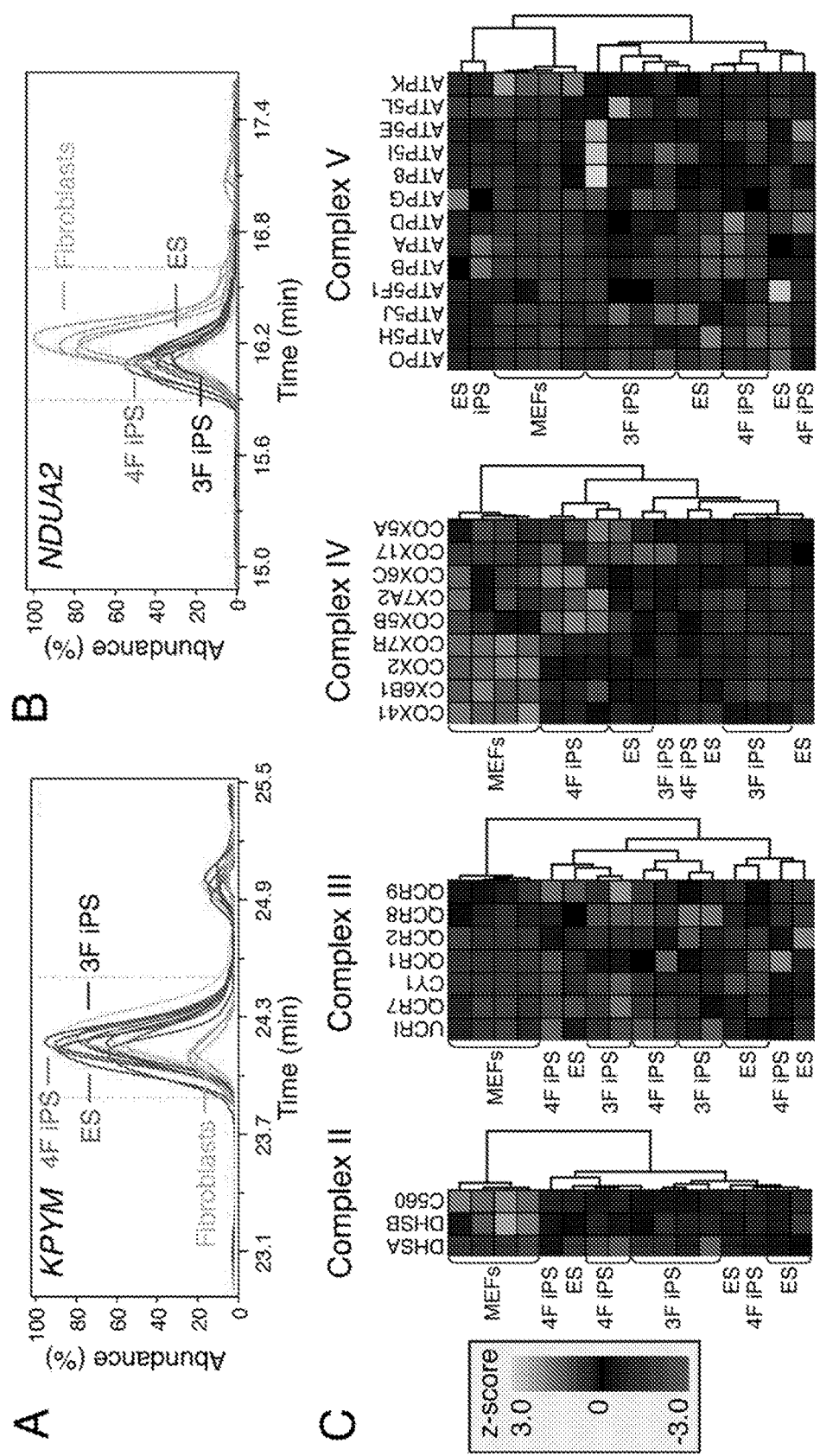
FIGS. 8A-C. Metabolic protein quantification demonstrates similar expression profiles for pluripotent cytotypes. Mass spectral features, following mass/charge and retention time alignment of all samples, were used for proteome-wide label-free quantification, as exemplified for glycolytic protein upregulation in (A) by pyruvate kinase (KPYM) and for electron transport chain complex I downregulation in (B) for NADH dehydrogenase 1 alpha subcomplex subunit 2 (NDUA2). (C) Heatmaps generated by agglomerative clustering of z-score transformed data for other electron transport chain complexes (II-V) demonstrated consistent expression profiles, clustering iPS cells and ESC away from MEFs within each complex. n=4 for each cell type. Flexibility in utilization of lactate and acetate was further supported in iPS cells that demonstrated selective upregulation of the mitochondrial form of aldehyde dehydrogenase and alcohol dehydrogenase class 3, with no changes in aldehyde dehydrogenase family 16 member A1 and alcohol dehydrogenase [NADP+].

Metaboproteome dissection revealed a transformed molecular signature in iPS cells, distinct from parental MEFs, yet synonymous to the metabolic protein profile of ES cells (FIGS. 4, G-J and 8, Table 1). A label-free proteomics approach revealed the identities of glycolytic enzymes consistently upregulated in pluripotent cytotypes relative to MEFs (FIGS. 4, G and 8, A), as confirmed by 2-DE analysis (FIG. 4, I). Conversely, 65% of complex 1 subunits were downregulated in iPS extracts (FIGS. 4, H and 8, B, and Table 1) as validated by 2-DE analysis (FIG. 4, J), indicating departure from MEF patterns and acquisition of a glycolytic-dependent profile (FIG. 4, K). In addition, reprogramming was associated with selective down regulation of the reducing equivalent entry points (complex I and II), as subunits of complex III and ATP synthase were upregulated in pluripotent cell types (FIG. 8, C and Table 1). Thus, the resolved iPS metaboproteome unmasks a targeted metabolic protein rearrangement underlying metabolic remodeling in nuclear reprogramming.

TABLE 1

Metabolic protein remodeling supports the iPS cell glycolytic metabotype.
Table S1 related to FIG. 4: Metabolic protein remodeling supports the iPSC glycolytic metabotype.

|  | Swiss Prot ID | Protein Abbrev | Protein Name | 4F iPSC versus MEF Ratio | 4F iPSC versus MEF P-value | 3F iPSC versus MEF Ratio | 3F iPSC versus MEF P-value |
|---|---|---|---|---|---|---|---|
| Glycolysis | P17710 | HXK1 | Hexokinase-1 | −2.58 | 1.62E−13 | −2.69 | 0.00E+00 |
|  | O08528 | HXK2 | Hexokinase-2 | 4.82 | 5.15E−18 | 3.63 | 0.00E+00 |
|  | P06745 | G6PI | Glucose-6-phosphate isomerase | −1.24 | 2.61E−03 | −1.40 | 1.98E−06 |
|  | P12382 | K6PL | 6-phosphofructokinase, liver type | 1.09 | 4.25E−01 | −1.06 | 5.97E−01 |
|  | Q9WUA3 | K6PP | 6-phosphofructokinase type C | 1.82 | 1.43E−15 | 3.29 | 0.00E+00 |
|  | Q2HYU2 | K6PF | 6-phosphofructokinase, muscle type | 3.95 | 1.21E−02 | 4.48 | 2.78E−03 |
|  | P05064 | ALDOA | Fructose-bisphosphate aldolase A | 1.01 | 9.02E−01 | 1.11 | 1.82E−01 |
|  | P09972 | ALDOC | Fructose-bisphosphate aldolase C | −1.00 | 9.70E−01 | 1.29 | 4.78E−02 |
|  | P17751 | TPIS | Triosephosphate isomerase | −1.17 | 1.81E−01 | −1.49 | 7.95E−04 |

TABLE 1-continued

Metabolic protein remodeling supports the iPS cell glycolytic metabotype.
Table S1 related to FIG. 4: Metabolic protein remodeling supports the iPSC glycolytic metabotype.

| | | | | | | | | |
|---|---|---|---|---|---|---|---|---|
| | | P16858 | GAPDH | Glyceraldehyde-3-phosphate dehydrogenase | 1.91 | 1.40E−45 | 1.74 | 5.17E−25 |
| | | P09411 | PGK1 | Phosphoglycerate kinase 1 | 1.11 | 1.76E−01 | 1.71 | 1.97E−17 |
| | | P18669 | PGAM1 | Phosphoglycerate mutase 1 | 3.37 | 1.41E−23 | 2.60 | 4.89E−09 |
| | | P17182 | ENOA | Alpha-enolase | 1.64 | 9.94E−27 | 1.14 | 1.90E−02 |
| | | Q3ZC09 | ENOB | Beta-enolase | 1.75 | 3.69E−03 | 1.38 | 5.74E−04 |
| | | P52480 | KPYM | Pyruvate kinase isozymes M1/M2 | 2.59 | 3.78E−03 | 2.29 | 9.20E−07 |
| | | P35486 | ODPA | Pyruvate dehydrogenase E1 component subunit alpha, somatic form | 2.31 | 1.94E−19 | 2.47 | 1.82E−29 |
| | | Q9D051 | ODPB | Pyruvate dehydrogenase E1 component subunit beta | 2.67 | 2.77E−22 | 2.82 | 1.78E−25 |
| | | Q8BMF4 | ODP2 | Dihydrolipoyllysine-residue acetyltransferase component of pyruvate dehydrogenase complex | −1.08 | 4.36E−01 | −1.36 | 7.21E−04 |
| | | P16125 | LDHB | L-lactate dehydrogenase B chain | 2.78 | 0.00E+00 | 3.18 | 0.00E+00 |
| | | P06151 | LDHA | L-lactate dehydrogenase A chain | 1.11 | 1.24E−01 | −1.13 | 1.16E−01 |
| | | Q15118 | PDK1 | Pyruvate dehydrogenase [lipoamide] kinase isozyme 1 | 4.12 | 3.04E−04 | 2.03 | 5.93E−02 |
| Oxidative Phosphorylation | Complex I | Q9CQ75 | NDUA2 | NADH dehydrogenase [ubiquinone] 1 alpha subcomplex subunit 2 | −1.79 | 1.45E−05 | −2.76 | 1.94E−11 |
| | | Q0MQ95 | NDUA3 | NADH dehydrogenase [ubiquinone] 1 alpha subcomplex subunit 3 | −2.80 | 1.53E−02 | −2.59 | 1.64E−02 |
| | | Q62425 | NDUA4 | NADH dehydrogenase [ubiquinone] 1 alpha subcomplex subunit 4 | 1.99 | 5.03E−03 | 2.00 | 8.66E−03 |
| | | P23935 | NDUA5 | NADH dehydrogenase [ubiquinone] 1 alpha subcomplex subunit 5 | −1.23 | 6.30E−01 | −1.37 | 4.41E−01 |
| | | Q9CQZ5 | NDUA6 | NADH dehydrogenase [ubiquinone] 1 alpha subcomplex subunit 6 | 1.65 | 1.09E−07 | 1.50 | 4.45E−05 |
| | | Q9DCJ5 | NDUA8 | NADH dehydrogenase [ubiquinone] 1 alpha subcomplex subunit 8 | 1.13 | 7.79E−01 | 1.19 | 6.80E−01 |
| | | Q9DC69 | NDUA9 | NADH dehydrogenase [ubiquinone] 1 alpha subcomplex subunit 9 | −7.38 | 4.33E−03 | −2.59 | 5.11E−02 |
| | | Q99LC3 | NDUAA | NADH dehydrogenase [ubiquinone] 1 alpha subcomplex subunit 10 | −1.69 | 2.74E−02 | −1.89 | 1.17E−02 |
| | | Q7TMF3 | NDUAC | NADH dehydrogenase [ubiquinone] 1 alpha subcomplex subunit 12 | −1.76 | 2.42E−02 | −3.09 | 1.55E−04 |
| | | Q9ERS2 | NDUAD | NADH dehydrogenase [ubiquinone] 1 alpha subcomplex subunit 13 | −4.43 | 2.85E−24 | −4.50 | 7.04E−27 |
| | | Q9CQZ6 | NDUB3 | NADH dehydrogenase [ubiquinone] 1 beta subcomplex subunit 3 | −1.61 | 2.20E−02 | −1.76 | 4.72E−03 |
| | | Q9CQC7 | NDUB4 | NADH dehydrogenase [ubiquinone] 1 beta subcomplex subunit 4 | −1.61 | 8.08E−02 | −1.63 | 7.62E−02 |
| | | Q9CQH3 | NDUB5 | NADH dehydrogenase [ubiquinone] 1 beta subcomplex subunit 5 | −2.10 | 1.32E−02 | −1.16 | 5.61E−01 |
| | | Q02368 | NDUB7 | NADH dehydrogenase [ubiquinone] 1 beta subcomplex subunit 7 | −2.06 | 8.25E−02 | −1.61 | 1.62E−01 |
| | | Q9DCS9 | NDUBA | NADH dehydrogenase [ubiquinone] 1 beta subcomplex subunit 10 | 1.26 | 2.54E−01 | 1.64 | 7.31E−04 |
| | | Q9CQ54 | NDUC2 | NADH dehydrogenase [ubiquinone] 1 subunit C2 | −3.09 | 2.86E−10 | −3.21 | 4.12E−10 |
| | | Q91VD9 | NDUS1 | NADH-ubiquinone oxidoreductase 75 kDa subunit | −1.18 | 4.21E−02 | −1.72 | 2.49E−17 |
| | | Q9DCT2 | NDUS3 | NADH dehydrogenase [ubiquinone] iron-sulfur protein 3 | −1.59 | 2.18E−04 | −2.21 | 3.90E−08 |
| | | Q9DC70 | NDUS7 | NADH dehydrogenase [ubiquinone] iron-sulfur protein 7 | −1.76 | 1.53E−02 | −2.72 | 4.58E−05 |
| | | P25708 | NDUV1 | NADH dehydrogenase [ubiquinone] flavoprotein 1 | 2.29 | 2.26E−05 | 1.84 | 4.18E−06 |
| | | Q9D6J6 | NDUV2 | NADH dehydrogenase [ubiquinone] flavoprotein 2 | 1.59 | 1.50E−01 | 1.34 | 3.46E−01 |
| | II | Q8K2B3 | DHSA | Succinate dehydrogenase [ubiquinone] flavoprotein subunit | 1.50 | 9.31E−08 | 1.60 | 1.39E−16 |
| | | Q9CQA3 | DHSB | Succinate dehydrogenase [ubiquinone] iron-sulfur subunit | −1.63 | 1.24E−02 | −1.89 | 1.54E−03 |
| | | Q9CZB0 | C560 | Succinate dehydrogenase cytochrome b560 subunit | −3.35 | 1.19E−09 | −2.34 | 3.61E−07 |
| | Complex III | Q9CZ13 | QCR1 | Cytochrome b-c1 complex subunit 1 | 2.87 | 6.79E−14 | 2.14 | 2.01E−20 |
| | | Q9DB77 | QCR2 | Cytochrome b-c1 complex subunit 2 | 1.71 | 1.89E−13 | 2.02 | 8.08E−17 |
| | | Q9D855 | QCR7 | Cytochrome b-c1 complex subunit 7 | 3.19 | 2.25E−06 | 3.47 | 1.97E−05 |
| | | O14949 | QCR8 | Cytochrome b-c1 complex subunit 8 | 1.03 | 8.69E−01 | 1.29 | 1.94E−02 |
| | | Q8R1I1 | QCR9 | Cytochrome b-c1 complex subunit 9 | −1.35 | 1.80E−01 | 1.11 | 5.01E−01 |
| | | Q9CR68 | UCRI | Cytochrome b-c1 complex subunit Rieske | 1.82 | 4.73E−05 | 1.89 | 1.94E−08 |
| | | Q9D0M3 | CY1 | Cytochrome c1, heme protein | 3.80 | 2.84E−11 | 4.40 | 3.79E−18 |
| | Complex IV | P19783 | COX41 | Cytochrome c oxidase subunit 4 isoform 1 | −1.90 | 5.19E−13 | −1.62 | 1.96E−09 |
| | | Q61387 | COX7R | Cytochrome c oxidase subunit 7A-related protein | −1.67 | 1.57E−03 | −2.23 | 1.18E−07 |
| | | P50672 | COX2 | Cytochrome c oxidase subunit 2 | −1.59 | 1.00E−08 | −2.06 | 2.37E−25 |
| | | P56391 | CX6B1 | Cytochrome c oxidase subunit VIb isoform 1 | −1.34 | 4.40E−02 | −1.91 | 1.38E−05 |
| | | Q9CPQ1 | COX6C | Cytochrome c oxidase polypeptide VIc | −1.16 | 2.62E−01 | −1.52 | 1.13E−05 |

TABLE 1-continued

Metabolic protein remodeling supports the iPS cell glycolytic metabotype.
Table S1 related to FIG. 4: Metabolic protein remodeling supports the iPSC glycolytic metabotype.

|  |  | P48771 | CX7A2 | Cytochrome c oxidase polypeptide 7A2 | −1.07 | 5.60E−01 | −1.42 | 1.39E−03 |
|---|---|---|---|---|---|---|---|---|
|  |  | P19536 | COX5B | Cytochrome c oxidase subunit 5B | 1.13 | 3.35E−01 | −1.23 | 7.26E−02 |
|  |  | P56394 | COX17 | Cytochrome c oxidase copper chaperone | 2.06 | 1.34E−03 | 1.84 | 2.07E−02 |
|  |  | P00426 | COX5A | Cytochrome c oxidase subunit 5A, mitochondrial | 2.13 | 1.40E−04 | 1.79 | 2.85E−03 |
| Complex V |  | P56135 | ATPK | ATP synthase subunit f | −2.28 | 8.54E−13 | −1.59 | 8.37E−06 |
|  |  | Q9CPQ8 | ATP5L | ATP synthase subunit g | −1.37 | 1.52E−02 | 1.06 | 6.54E−01 |
|  |  | P03930 | ATP8 | ATP synthase protein 8 | −1.28 | 3.47E−02 | 1.04 | 7.92E−01 |
|  |  | Q06185 | ATP5I | ATP synthase subunit e | 1.02 | 8.99E−01 | 1.46 | 1.16E−03 |
|  |  | Q9CQQ7 | AT5F1 | ATP synthase subunit b | 1.08 | 3.36E−01 | 1.16 | 1.22E−02 |
|  |  | P29418 | ATP5E | ATP synthase subunit epsilon | 1.32 | 9.06E−02 | 1.29 | 1.61E−01 |
|  |  | P97450 | ATP5J | ATP synthase-coupling factor 6 | 1.54 | 1.35E−02 | 1.88 | 5.23E−05 |
|  |  | Q91VR2 | ATPG | ATP synthase subunit gamma | 1.57 | 7.73E−09 | 1.85 | 2.20E−13 |
|  |  | Q9DCX2 | ATP5H | ATP synthase subunit d | 1.74 | 3.76E−04 | 1.85 | 6.03E−16 |
|  |  | Q9DB20 | ATPO | ATP synthase subunit O | 1.76 | 2.81E−06 | 2.15 | 9.85E−17 |
|  |  | P56480 | ATPB | ATP synthase subunit beta | 1.90 | 1.43E−09 | 1.80 | 5.27E−21 |
|  |  | P35434 | ATPD | ATP synthase subunit delta | 1.96 | 2.53E−09 | 1.63 | 2.28E−10 |
|  |  | Q03265 | ATPA | ATP synthase subunit alpha | 2.06 | 6.86E−21 | 1.86 | 1.72E−35 |

|  |  | Swiss Prot ID | ESC versus MEF | | ESC versus 4F iPSC | | ESC versus 3F iPSC | | 4F iPSC versus 3F iPSC | |
|---|---|---|---|---|---|---|---|---|---|---|
|  |  |  | Ratio | P-value | Ratio | P-value | Ratio | P-value | Ratio | P-value |
| Glycolysis |  | P17710 | −2.67 | 2.12E−37 | −1.04 | 8.72E−01 | 1.01 | 9.46E−01 | 1.05 | 8.32E−01 |
|  |  | O08528 | 3.61 | 1.70E−27 | −1.34 | 1.51E−02 | −1.01 | 9.45E−01 | 1.33 | 1.06E−02 |
|  |  | P06745 | −1.48 | 5.71E−08 | −1.19 | 1.93E−02 | −1.06 | 4.48E−01 | 1.13 | 1.01E−01 |
|  |  | P12382 | 1.61 | 7.97E−07 | 1.48 | 2.60E−04 | 1.70 | 2.27E−07 | 1.15 | 2.30E−01 |
|  |  | Q9WUA3 | 1.58 | 1.46E−24 | −1.15 | 3.82E−02 | −2.08 | 1.43E−28 | −1.81 | 4.78E−17 |
|  |  | Q2HYU2 | 3.96 | 8.42E−03 | 1.00 | 9.94E−01 | −1.13 | 7.13E−01 | −1.14 | 7.15E−01 |
|  |  | P05064 | 1.12 | 2.00E−01 | 1.11 | 1.94E−01 | 1.01 | 8.87E−01 | −1.09 | 1.63E−01 |
|  |  | P09972 | 1.16 | 1.58E−01 | 1.17 | 1.25E−01 | −1.11 | 4.29E−01 | −1.30 | 3.78E−02 |
|  |  | P17751 | −1.02 | 8.41E−01 | 1.15 | 2.29E−01 | 1.45 | 7.16E−04 | 1.27 | 3.85E−02 |
|  |  | P16858 | 2.21 | 1.17E−13 | 1.16 | 6.34E−02 | 1.27 | 4.28E−03 | 1.10 | 1.66E−02 |
|  |  | P09411 | −1.04 | 6.85E−01 | −1.15 | 6.75E−02 | −1.77 | 2.45E−20 | −1.54 | 7.47E−14 |
|  |  | P18669 | 2.81 | 3.37E−13 | −1.20 | 8.88E−02 | 1.08 | 5.53E−01 | 1.30 | 2.67E−02 |
|  |  | P17182 | 1.47 | 2.51E−15 | −1.12 | 2.69E−03 | 1.29 | 1.71E−09 | 1.44 | 1.79E−19 |
|  |  | Q3ZC09 | 1.66 | 2.00E−08 | −1.05 | 7.55E−01 | 1.21 | 4.99E−02 | 1.27 | 1.72E−01 |
|  |  | P52480 | 2.90 | 2.63E−07 | 1.12 | 6.43E−01 | 1.26 | 1.78E−01 | 1.13 | 6.22E−01 |
|  |  | P35486 | 2.21 | 1.14E−16 | −1.05 | 6.10E−01 | 1.12 | 1.47E−01 | −1.07 | 3.61E−01 |
|  |  | Q9D051 | 2.75 | 1.36E−14 | 1.03 | 7.38E−01 | −1.02 | 7.92E−01 | −1.06 | 4.58E−01 |
|  |  | Q8BMF4 | −1.25 | 1.83E−02 | −1.16 | 1.51E−01 | 1.09 | 3.38E−01 | 1.27 | 1.86E−02 |
|  |  | P16125 | 2.60 | 3.09E−30 | −1.07 | 2.71E−01 | −1.22 | 5.50E−05 | −1.14 | 1.26E−03 |
|  |  | P06151 | 1.22 | 3.68E−03 | 1.10 | 2.36E−02 | 1.38 | 2.41E−12 | 1.25 | 4.80E−08 |
|  |  | Q15118 | 3.67 | 2.87E−04 | −1.12 | 6.59E−01 | 1.81 | 3.04E−02 | 2.02 | 1.80E−02 |
| Oxidative Phosphorylation | Complex I | Q9CQ75 | −3.37 | 4.19E−14 | −1.88 | 9.53E−05 | −1.22 | 2.44E−01 | 1.54 | 4.90E−03 |
|  |  | Q0MQ95 | −2.35 | 3.29E−02 | 1.19 | 6.77E−01 | 1.10 | 7.94E−01 | −1.08 | 8.35E−01 |
|  |  | Q62425 | 2.02 | 7.69E−03 | 1.01 | 9.18E−01 | 1.01 | 9.49E−01 | −1.00 | 9.76E−01 |
|  |  | P23935 | −1.37 | 4.64E−01 | −1.12 | 7.61E−01 | −1.01 | 9.84E−01 | 1.11 | 7.47E−01 |
|  |  | Q9CQZ5 | 1.52 | 9.81E−06 | −1.09 | 3.21E−01 | 1.01 | 8.82E−01 | 1.10 | 2.68E−01 |
|  |  | Q9DCJ5 | 1.02 | 9.64E−01 | −1.10 | 6.09E−01 | −1.16 | 4.45E−01 | −1.05 | 7.39E−01 |
|  |  | Q9DC69 | −3.09 | 2.90E−02 | 2.39 | 5.64E−02 | −1.19 | 6.39E−01 | −2.85 | 2.90E−02 |
|  |  | Q99LC3 | −1.59 | 3.35E−02 | 1.06 | 7.89E−01 | 1.18 | 4.74E−01 | 1.12 | 6.79E−01 |
|  |  | Q7TMF3 | −3.00 | 2.21E−04 | −1.70 | 7.32E−02 | 1.03 | 9.31E−01 | 1.75 | 5.73E−02 |
|  |  | Q9ERS2 | −4.66 | 5.11E−24 | −1.05 | 7.95E−01 | −1.03 | 8.38E−01 | 1.02 | 9.05E−01 |
|  |  | Q9CQZ6 | −2.61 | 2.78E−05 | −1.62 | 7.73E−02 | −1.48 | 1.17E−01 | 1.09 | 7.09E−01 |
|  |  | Q9CQC7 | −2.05 | 1.77E−02 | −1.27 | 2.98E−01 | −1.25 | 3.43E−01 | 1.01 | 9.46E−01 |
|  |  | Q9CQH3 | −2.39 | 9.13E−04 | −1.14 | 7.72E−01 | −2.07 | 4.79E−02 | −1.81 | 1.27E−01 |
|  |  | Q02368 | −2.06 | 8.06E−02 | 1.00 | 9.96E−01 | −1.28 | 5.21E−01 | −1.28 | 5.24E−01 |
|  |  | Q9DCS9 | 1.01 | 9.56E−01 | −1.25 | 3.30E−01 | −1.62 | 4.86E−03 | −1.30 | 1.37E−01 |
|  |  | Q9CQ54 | −4.30 | 6.81E−13 | −1.39 | 1.92E−01 | −1.34 | 2.90E−01 | 1.04 | 8.68E−01 |
|  |  | Q91VD9 | −1.71 | 2.64E−21 | −1.45 | 7.92E−05 | 1.01 | 9.21E−01 | 1.46 | 1.55E−04 |
|  |  | Q9DCT2 | −1.77 | 7.20E−05 | −1.11 | 5.57E−01 | 1.25 | 2.91E−01 | 1.39 | 7.13E−02 |
|  |  | Q9DC70 | −2.29 | 6.25E−04 | −1.30 | 4.07E−01 | 1.19 | 5.98E−01 | 1.54 | 1.76E−01 |
|  |  | P25708 | 1.58 | 4.04E−03 | −1.45 | 2.81E−02 | −1.16 | 2.26E−01 | 1.25 | 1.43E−01 |
|  |  | Q9D6J6 | 1.58 | 2.11E−01 | −1.00 | 9.90E−01 | 1.19 | 6.30E−01 | 1.19 | 5.83E−01 |
|  | II | Q8K2B3 | 1.51 | 2.05E−10 | 1.01 | 9.06E−01 | −1.06 | 2.21E−01 | −1.07 | 2.44E−01 |
|  |  | Q9CQA3 | −1.87 | 3.30E−03 | −1.15 | 5.04E−01 | 1.01 | 9.54E−01 | 1.16 | 4.17E−01 |
|  |  | Q9CZB0 | −3.22 | 9.00E−09 | 1.04 | 8.85E−01 | −1.37 | 1.63E−01 | −1.43 | 9.32E−02 |
|  | Complex III | Q9CZ13 | 2.66 | 5.49E−34 | −1.08 | 4.36E−01 | 1.24 | 3.45E−03 | 1.34 | 7.59E−03 |
|  |  | Q9DB77 | 2.18 | 2.71E−13 | 1.27 | 3.86E−03 | 1.08 | 3.69E−01 | −1.18 | 1.25E−02 |
|  |  | Q9D855 | 3.05 | 1.33E−04 | −1.05 | 7.94E−01 | −1.14 | 5.07E−01 | −1.09 | 6.25E−01 |
|  |  | O14949 | −1.01 | 9.39E−01 | −1.04 | 8.25E−01 | −1.31 | 2.65E−02 | −1.26 | 7.67E−02 |
|  |  | Q8R1I1 | −1.23 | 3.01E−01 | −1.09 | 7.74E−01 | −1.37 | 1.64E−01 | −1.50 | 9.93E−02 |
|  |  | Q9CR68 | 1.41 | 4.53E−02 | −1.29 | 6.31E−02 | −1.34 | 8.86E−03 | −1.04 | 7.09E−01 |
|  |  | Q9DOM3 | 4.10 | 5.74E−09 | 1.08 | 6.44E−01 | −1.07 | 6.34E−01 | −1.16 | 2.67E−01 |

TABLE 1-continued

Metabolic protein remodeling supports the iPS cell glycolytic metabotype.
Table S1 related to FIG. 4: Metabolic protein remodeling supports the iPSC glycolytic metabotype.

| | | | | | | | | | |
|---|---|---|---|---|---|---|---|---|---|
| Complex IV | P19783 | −2.02 | 2.83E−12 | −1.06 | 6.49E−01 | −1.24 | 6.59E−02 | −1.17 | 1.23E−01 |
| | Q61387 | −1.65 | 1.72E−03 | 1.01 | 9.51E−01 | 1.35 | 1.67E−01 | 1.34 | 1.97E−01 |
| | P50672 | −1.61 | 4.19E−08 | −1.01 | 9.33E−01 | 1.28 | 3.68E−02 | 1.29 | 1.87E−02 |
| | P56391 | −1.49 | 3.28E−03 | −1.11 | 5.35E−01 | 1.28 | 1.45E−01 | 1.43 | 5.87E−02 |
| | Q9CPQ1 | −1.30 | 4.30E−04 | −1.13 | 3.88E−01 | 1.16 | 1.25E−01 | 1.31 | 9.04E−02 |
| | P48771 | −1.23 | 6.22E−02 | −1.14 | 3.17E−01 | 1.16 | 2.25E−01 | 1.32 | 4.05E−02 |
| | P19536 | 1.00 | 9.75E−01 | −1.13 | 3.40E−01 | 1.24 | 5.70E−02 | 1.39 | 3.29E−03 |
| | P56394 | 2.18 | 7.72E−04 | 1.06 | 7.62E−01 | 1.18 | 4.26E−01 | 1.12 | 5.93E−01 |
| | P00426 | 1.96 | 1.01E−03 | −1.09 | 4.83E−01 | 1.09 | 4.31E−01 | 1.19 | 1.20E−01 |
| Complex V | P56135 | −2.04 | 4.43E−08 | 1.12 | 4.75E−01 | −1.28 | 6.71E−02 | −1.43 | 8.83E−04 |
| | Q9CPQ8 | −1.26 | 1.30E−01 | 1.09 | 6.55E−01 | −1.33 | 1.03E−01 | −1.45 | 2.02E−02 |
| | P03930 | −1.27 | 3.20E−02 | 1.01 | 9.53E−01 | −1.32 | 1.22E−01 | −1.33 | 1.19E−01 |
| | Q06185 | 1.11 | 3.40E−01 | 1.10 | 5.27E−01 | −1.31 | 3.35E−02 | −1.43 | 9.80E−03 |
| | Q9CQQ7 | 1.24 | 5.40E−02 | 1.15 | 1.88E−01 | 1.07 | 4.89E−01 | −1.08 | 1.86E−01 |
| | P29418 | 1.20 | 2.03E−01 | −1.09 | 4.94E−01 | −1.07 | 6.44E−01 | 1.02 | 9.00E−01 |
| | P97450 | 1.69 | 8.51E−03 | 1.10 | 6.12E−01 | −1.11 | 5.07E−01 | −1.22 | 1.76E−01 |
| | Q91VR2 | 1.93 | 2.00E−11 | 1.23 | 1.63E−02 | 1.04 | 6.42E−01 | −1.18 | 2.79E−02 |
| | Q9DCX2 | 2.02 | 1.57E−06 | 1.16 | 3.09E−01 | 1.09 | 4.31E−01 | −1.07 | 5.74E−01 |
| | Q9DB20 | 2.07 | 7.72E−07 | 1.17 | 1.92E−01 | −1.04 | 6.88E−01 | −1.22 | 1.66E−02 |
| | P56480 | 1.92 | 5.46E−23 | 1.01 | 9.01E−01 | 1.07 | 2.97E−01 | 1.06 | 5.43E−01 |
| | P35434 | 1.75 | 2.93E−05 | −1.12 | 3.25E−01 | 1.08 | 4.73E−01 | 1.21 | 3.01E−02 |
| | Q03265 | 2.03 | 2.63E−29 | −1.01 | 8.35E−01 | 1.09 | 1.04E−01 | 1.11 | 1.07E−01 |

The results provided herein demonstrate that regression of mitochondria to an embryonic like state and metaboproteome restructuring underlied a distinctive metabolic switch from somatic oxidative metabolism of parental fibroblasts to glycolysis of derived pluripotency progeny. Indeed, promotion of glycolysis away from oxidative metabolism controlled the efficiency of nuclear reprogramming. The regression of the parental somatic network of abundant tubular and cristae-rich mitochondria into sparse spherical and cristae-poor structures characterized iPS progeny. Metabolomic footprinting and fingerprinting demonstrated distinct changes in iPS cell metabolism. The key metabolic rates contributing to the iPS phenotype were consistent among multiple clones, and included elevated utilization of glucose and accumulation of both lactate and acetate. Compared to MEFs, iPS cells demonstrated reduced oxygen consumption and diminished capacity to increase oxygen utilization in response to electron transport chain uncoupling. These results suggest a departure from, albeit not elimination of, oxidative metabolism with induced pluripotency.

As demonstrated herein, inhibition of glycolytic flux and stimulation of oxidative metabolism, either pharmacologically or through extracellular glucose removal, impaired reprogramming while stimulating glycolytic flux by elevated glucose availability potentiated reprogramming. Of note, media supplemented with glutamate and pyruvate was sufficient to support growth of parental fibroblasts, with supplemented glucose available for anabolic processes during reprogramming. Modification of the catabolic/anabolic balance during reprogramming thus impacts pluripotent induction.

Taken together, the results provided herein demonstrate that induction of a functional pluripotent glycolytic metabotype, with limited dependence on mitochondrial metabolism, precedes and is required for successful nuclear reprogramming. Dedifferentiation of parental somatic cells regressed mitochondrial morphology, downregulated electron transport chain subunits, and upregulated glycolytic enzymes. The acquired metabolic infrastructure supported the anabolic and catabolic requirements for bona fide pluripotency, defining the glycolytic signature of bioengineered iPS cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for augmenting production of induced pluripotent stem cells being produced from isolated somatic cells by contacting said isolated somatic cells with stemness transcription factors, wherein said stemness transcription factors comprise OCT3/4, SOX2, and KLF4, wherein said method comprises culturing said isolated somatic cells in medium comprising about 12.5 mM of glucose to produce said induced pluripotent stem cells.

2. The method of claim 1, wherein said somatic cells are fibroblasts.

3. The method of claim 1, wherein said stemness transcription factors further comprise c-MYC.

* * * * *